US012746126B2

(12) United States Patent
Medoff

(10) Patent No.: US 12,746,126 B2
(45) Date of Patent: Sep. 29, 2026

(54) IMPLANT FOR FUSING AT LEAST TWO BONE COMPONENTS AND METHOD OF FUSING BONE COMPONENTS USING THE IMPLANT

(71) Applicant: TriMed, Incorporated, Santa Clarita, CA (US)

(72) Inventor: Robert Medoff, Kailua, HI (US)

(73) Assignee: TriMed, Inc., Santa Clarita, CA (US)

(*) Notice: Subject to any disclaimer, the term of this patent is extended or adjusted under 35 U.S.C. 154(b) by 1329 days.

(21) Appl. No.: 17/168,759

(22) Filed: Feb. 5, 2021

(65) Prior Publication Data

US 2021/0244542 A1 Aug. 12, 2021

Related U.S. Application Data

(60) Provisional application No. 62/971,482, filed on Feb. 7, 2020.

(51) Int. Cl.
*A61F 2/42* (2006.01)
*A61B 17/72* (2006.01)
(Continued)

(52) U.S. Cl.
CPC .............. *A61F 2/30* (2013.01); *A61F 2/4606* (2013.01); *A61B 17/72* (2013.01);
(Continued)

(58) Field of Classification Search
CPC .. A61F 2/4604; A61F 2/30; A61F 2002/2835; A61F 2002/30131;
(Continued)

(56) References Cited

U.S. PATENT DOCUMENTS 5,180,384 A * 1/1993 Mikhail ............. A61B 17/1659 606/80
6,179,839 B1 * 1/2001 Weiss ................ A61B 17/8061 606/85

(Continued)

OTHER PUBLICATIONS

Synonyms for "cup-shaped" retrieved from thesaurus.com on Apr. 21, 2026. (Year: 2026).*

(Continued)

*Primary Examiner* — Megan Y Wolf
(74) *Attorney, Agent, or Firm* — Wood, Phillips, Katz, Clark & Mortimer

(57) ABSTRACT

An implant for fusing at least two bone components and method of using the implant. The implant has a body with first and second anchoring portions. The first anchoring portion has a stem configured to be directed to within a first bone component and is further configured to cooperate with at least a first fastener usable to fix the stem in an operative position relative to the first bone component. The second anchoring portion is configured to overlie at least a second bone component at a placement location at which bone has been strategically removed and is further configured to cooperate with at least a second fastener usable to fix a part of the second anchoring portion to the second bone component with the second anchoring portion in an operative position.

51 Claims, 15 Drawing Sheets

(51) Int. Cl.

| | |
|---|---|
| ***A61B 17/80*** | (2006.01) |
| ***A61F 2/30*** | (2006.01) |
| ***A61F 2/46*** | (2006.01) |
| *A61F 2/28* | (2006.01) |

(52) U.S. Cl.
CPC ........... *A61B 17/7291* (2013.01); *A61B 17/80* (2013.01); *A61F 2002/2835* (2013.01); *A61F 2002/30131* (2013.01); *A61F 2002/30622* (2013.01); *A61F 2002/30777* (2013.01); *A61F 2002/30787* (2013.01); *A61F 2002/30805* (2013.01); *A61F 2002/4205* (2013.01); *A61F 2002/4212* (2013.01); *A61F 2002/4264* (2013.01); *A61F 2002/4269* (2013.01); *A61F 2002/4271* (2013.01); *A61F 2310/00011* (2013.01)

(58) Field of Classification Search
CPC .. A61F 2002/30622; A61F 2002/30777; A61F 2002/30787; A61F 2002/30805; A61F 2002/4205; A61F 2002/4212; A61F 2002/1269; A61F 2002/4271; A61F 2310/00011; A61B 17/7291
See application file for complete search history.

(56) References Cited

U.S. PATENT DOCUMENTS

| | | | | |
|---|---|---|---|---|
| 2002/0143337 | A1* | 10/2002 | Orbay ................ | A61B 17/7208 606/62 |
| 2010/0010490 | A1* | 1/2010 | Brigido .............. | A61B 17/1775 606/62 |
| 2010/0130978 | A1* | 5/2010 | Orbay ................... | A61F 2/4261 606/62 |
| 2013/0289738 | A1* | 10/2013 | Humphrey ................ | A61F 2/30 623/23.42 |
| 2015/0100132 | A1 | 4/2015 | Vanasse et al. | |
| 2015/0112343 | A1* | 4/2015 | Medoff .............. | A61B 17/8061 606/64 |
| 2016/0354127 | A1* | 12/2016 | Lundquist .......... | A61B 17/8061 |
| 2017/0290670 | A1* | 10/2017 | Gorelick ............... | A61F 2/4261 |
| 2017/0296350 | A1 | 10/2017 | Orbay et al. | |
| 2019/0358046 | A1* | 11/2019 | Ehmke ............... | A61B 17/1775 |
| 2021/0030451 | A1* | 2/2021 | Muller ............... | A61B 17/8023 |

OTHER PUBLICATIONS

International Search Report and Written Opinion, mailed May 4, 2021 in International Patent Application No. PCT/US21/16817.

* cited by examiner

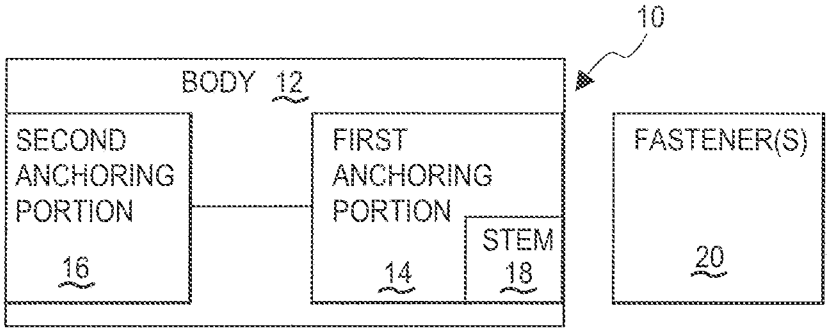
Fig. 1
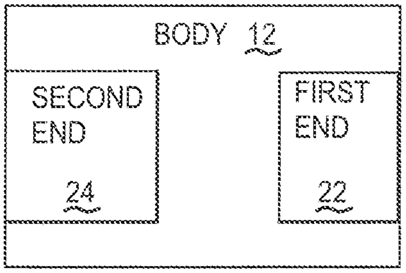
Fig. 2
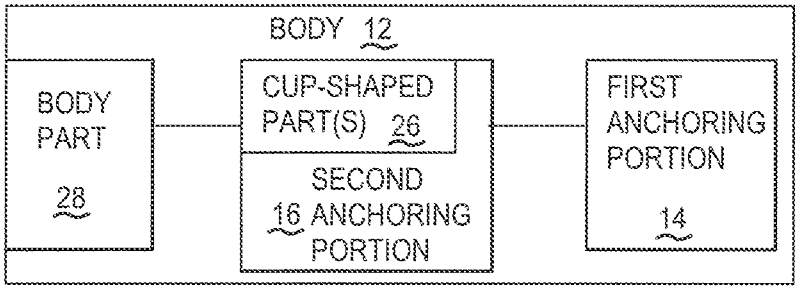
Fig. 3
Fig. 4
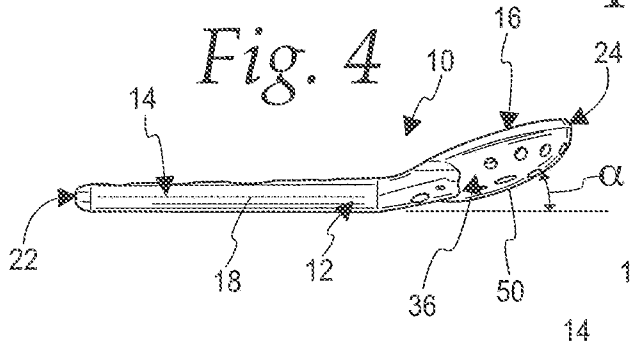
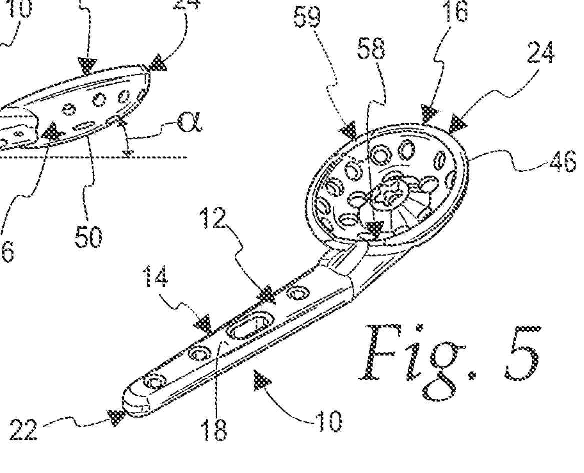
Fig. 5

*Fig. 18*
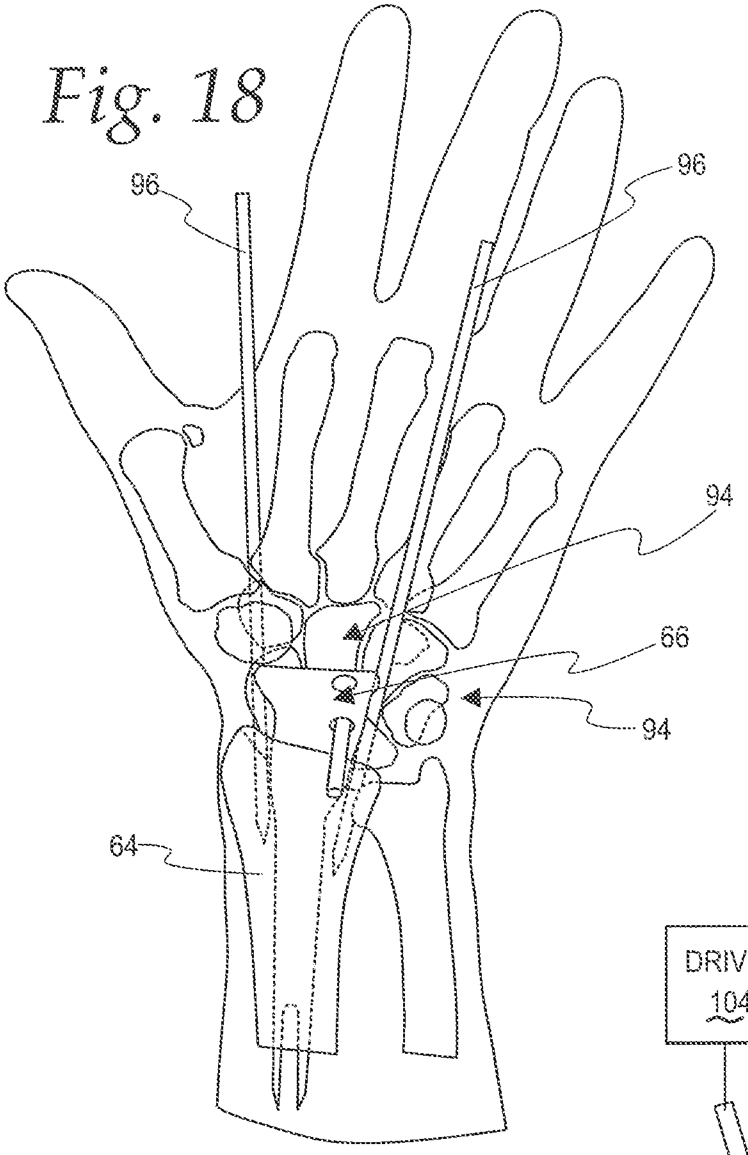
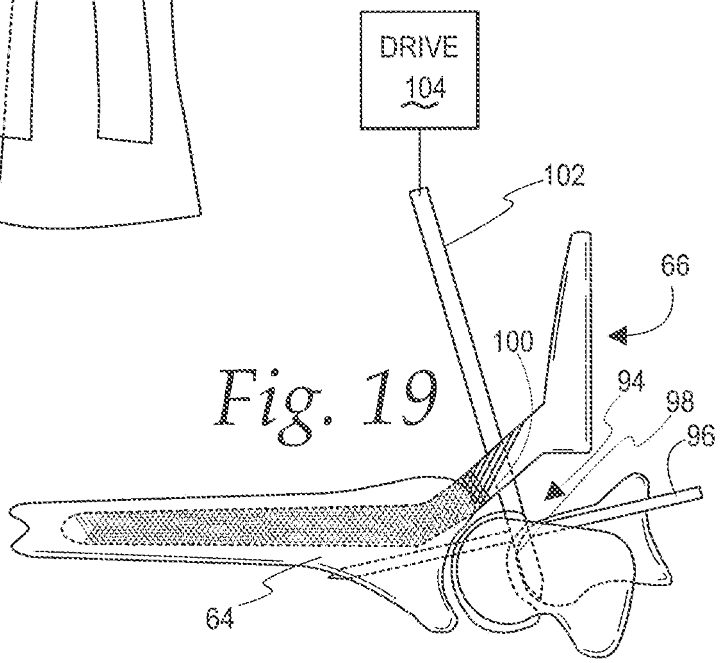
*Fig. 19*

IMPLANT FOR FUSING AT LEAST TWO BONE COMPONENTS AND METHOD OF FUSING BONE COMPONENTS USING THE IMPLANT

BACKGROUND OF THE INVENTION

Field of the Invention

This invention relates to medical implants and, more particularly, to an implant for fusing separate bones/bone components. The invention is also directed to a method of using the implant to effect fusion of bone components.

Background Art

Joint arthritis results in limited motion, pain, and dysfunction and can affect any joint in the human body. One option for treating pain is joint fusion, which involves roughening bone surfaces and applying some type of fixation to hold separate bone components rigidly fixed in apposition until they heal as a single block. Although successful fusion eliminates relative movement between bone components/bones at a joint, this procedure can be very effective in resolving most, if not all, of the arthritic pain.

The invention herein can be applied to any joint in the body in which one bone has a tubular portion. For purposes of example, the wrist will be used throughout this document, in terms of describing the prior art and the present invention, but is provided by way of example only and should not imply any anatomic limitation.

The wrist contains multiple small bones, resulting in difficulties in individually fixing these bones and providing adequate screw fixation. In addition, the wrist has multiple tendons in close apposition to the bones in this area. Implants can irritate or damage these structures resulting in stiffness, pain, inflammation, and even rupture. The wrist is a highly mobile joint and subject to strong forces which can produce significant bending loads from the pull of tendons that cross the joint.

In general, there are four main types of contemporary implants used for providing fixation when doing a joint arthrodesis or fusion: external fixation; spanning plates; intramedullary nails; and circular cups.

External fixation immobilizes the joint with an external bar that is fixed to a cluster of one or more pins placed in bones on either side of the joint. This method is usually not preferred for several reasons, including possible infection, tendon irritation, inability to rigidly secure bones in between the pin clusters, pain, non-unions, and others.

Spanning plates are internal implants that screw into the bones on either side of the joint, and sometimes the intermediate bones in the joint. The most commonly accepted plate for wrist fusions spans from the radial bone in the forearm to one of the metacarpals in the hand. Plates of this type are offset from the central, neutral axis of bone, which places them at a further mechanical disadvantage. They need to be fairly thick to resist the normal torque and bending moments, resulting in a bulky surface implant that can often result in soft tissue irritation, cosmetic prominence, and even tendon rupture. Because of the curved shape of the bone surface as it extends from the distal radius across the carpus, these plates are typically formed with a complex curvilinear shape to maintain apposition of the hardware to the bone over the length of the plate. Often these shapes do not precisely fit a specific anatomy and may be prominent or necessitate extensive modification of the bone surfaces.

Since the plate is secured to the metacarpal, which is a narrow bone, screw holes in the bone can lead to secondary fracture and result in morbidity and secondary surgical procedures. Furthermore, fixation to the metacarpals results in the plate spanning the carpometacarpal joints, which are typically not damaged and do not require fusion. These plates are incapable of, or ineffective in, including fixation to the intermediate carpal bones, as some are located beyond the lateral border of the plate. With this type of implant it is nearly impossible to ensure that screw holes will be optimally located under each carpal bone involved in the fusion. Heavy surface plates cause stress shielding and disuse osteoporosis which may lead to fracture at either end of the plate. Finally, the plates can be prominent and cause a cosmetic issue.

An alternative to spanning plate fixation is a non-spanning plate. This type of device is similar to the spanning plate but does not cross the carpometacarpal joints, thereby avoiding the problems caused by metacarpal fixation. Instead, the plate widens at its distal end and screws are placed into several of the carpal bones. This type of plate design, however, still has the other shortcomings associated with spanning plates, including: the offset of fixation from the central, neutral axis of bone; need for enough plate bulk and thickness to overcome bending loads; surface prominence and soft tissue irritation; and tendon problems. In addition, however, it introduces yet other issues.

Because this design does not extend to the metacarpal, it has only a limited lever arm at its distal purchase of the fusion mass and for this reason is subject to larger loads than a spanning plate. Most designs offer a flared, widened distal end to allow screws in multiple planes to purchase various carpal bones. However, screw holes may not align with the optimal purchase sites on the carpal bones. This implant still requires the surgeon to tediously decorticate both joint surfaces as well as the superficial bone surfaces in order to provide a rich, raw bed of bone to promote fusion. These plates are applied to the surface of the bone and have a certain degree of surface prominence which may still cause soft tissue irritation. Finally, most of these plates still require a complex curvature to match the surface of the bone, or require the surgeon to effectively be a skilled carpenter and make a precision cut out of a flat channel to match the plate contour so the plate can be recessed within the bone.

Yet another implant option for wrist fusion is an intramedullary device that extends from the intramedullary canal of the distal radius, across the carpus, and into the intramedullary canal of one of the metacarpals. Although this concept has a theoretical advantage of removing hardware from the surface of the bone and placing the implant close to the central, neutral axis of bone, it introduces a significant number of other problems that have severely limited its acceptance into clinical use.

First, the canal of the metacarpals is quite narrow, limiting both the size of the implant as well as the size of the interlocking screws used to secure the implant—both of which increase the risk of implant failure. Adding screws to this narrow intramedullary nail further weakens it. Second, because of the anatomy, it is impossible to place a one piece intramedullary nail across the wrist. Since the wrist is typically fused in 0° to 30° of extension, implanting a nail in this position requires two pieces that are coupled together once the separate intramedullary components are implanted on either side of the joint. The coupling mechanism is awkward, adds small intermediate components that further weaken the device, is difficult to apply, may fail due to insufficient strength, and adds additional bulk between bones that the surgeon is trying to fuse. Third, once the wrist is fused, these implants are nearly impossible to remove without extensive destruction of the bone. If the wrist gets an infection and removal is required, the surgeon is faced with cutting open the bone canals to remove the implant. The surgical technique for this implant is difficult and technically challenging.

Metal or Polyetheretherketone (PEEK) circular, or partially circular, cups have been used successfully for partial intercarpal fusions that limit the number of carpal bones. Examples include four corner fusions that fuse the capitate, hamate, lunate, and triquetral bones, scapho-trapezium-trapezoid fusions, midcarpal fusions, or the radio-scapho-lunate fusion that fuses the radius to the scaphoid and lunate. These are also done for bones in the foot as well. In this procedure, the joint surfaces are first decorticated as with any fusion. A hemispherically curved power reamer is then used to create a cup-shaped trough recessed within the surface of the bone. This easily and quickly creates a raw, vascular bone bed conducive for producing a fusion mass of new bone across the joint, and is matched to at least a portion of the curvature of the cup to improve fixation stability. In addition, the PEEK cup has several other advantages. It is more isoelastic to cortical bone in terms of stiffness, so has less stress shielding than metal plates. The cup-shaped design has a natural rigidity, effectively improving the resistance bending load due to the three dimensional structural form while allowing the use of a thinner implant. Some designs provide polyaxial locking screws for plate fixation. This allows variation in the direction over a range of angles and creates an angular lock to the plate which adds to stiffness and stability. This type of design makes it easier for the surgeon to direct each screw in an optimal direction into the underlying carpal bone. PEEK cups are also radiolucent, thereby allowing the surgeon to visualize the accuracy of screw position, implant and bone position, and bone apposition on x-ray.

Currently, PEEK cups are predominantly used for partial wrist fusions. Because of the high bending loads at the wrist, they have had limited use when applied for total wrist fusion or fusion of the proximal carpal row to the radius. Circular cups spans only a limited distance, providing a short lever arm to resist the large bending loads that occur across the wrist. Further, if considered for a total wrist fusion, the circular cup would need to be excessively large in diameter. In addition to creating an awkward, bulky implant that would be difficult to apply, it would physically extend the span of the implant, causing interference with motion of the distal radioulnar joint.

The medical industry continues to seek out alternative implant designs and fusion methods to address one or more of the problems or shortcomings described above.

SUMMARY OF THE INVENTION

In one form, the invention is directed to an implant for fusing at least two bone components. The implant has a body with first and second anchoring portions. The first anchoring portion has a stem configured to be directed to within a first bone component with the first anchoring portion in an operative position. The first anchoring portion is configured to cooperate with at least a first fastener usable to cause the stem to be fixed relative to the first bone component with the first anchoring portion in its operative position. The second anchoring portion is configured to be fixed to at least a second bone component. The second anchoring portion is configured such that when in an operative position at least a portion of the second anchoring portion lies within a cavity produced in the at least second bone. The second anchoring portion is further configured to cooperate with at least a second fastener usable to fix a part of the second anchoring portion relative to the second bone component to thereby maintain the second anchoring portion in its operative position.

In one form, the stem has an opening therein to cooperate with the first fastener usable to fix the stem relative to the first bone component and thereby maintain the first anchoring portion in its operative position.

In one form, the implant is provided in combination with the first fastener configured to extend into the first bone component and the stem opening to fix the stem relative to the first bone component.

In one form, the second anchoring portion has an opening therein through which the second fastener can extend to be directed into the second bone component to fix the part of the second anchoring portion relative to the second bone component.

In one form, the implant is provided in further combination with the second fastener configured to extend through the opening in the second anchoring portion and into the second bone component to fix the part of the second anchoring portion relative to the second bone component.

In one form, the body has a single rigid piece that defines the first and second anchoring portions.

In one form, the body has an elongate shape with a length between first and second ends and a width. The stem extends to the first body end and the second anchoring portion is at the second body end.

In one form, a surface on the second anchoring portion that extends into the cavity with the second anchoring portion in its operative position has at least a portion with a convex shape.

In one form, the second anchoring portion has a cup-shaped surface.

In one form, the cup-shaped surface has a central axis. The body has an elongate portion defining the stem. The elongate portion extends away from the part of the second anchoring portion and has a lengthwise center line. The lengthwise center line is offset from the central axis.

In one form, the cup-shaped surface extends to a rim. There is a discrete cutout through the rim.

In one form, at least a part of the second anchoring portion has a cup-shaped wall.

In one form, the cup-shaped wall has a central axis. A convex outer surface defines the surface on the second anchoring part that extends into the cavity. The convex outer surface is symmetrical around the central axis and tapers in an axial direction.

In one form, the cup-shaped wall has a plurality of openings through which fasteners can be directed at different angles.

In one form, the cup-shaped wall has a discrete receptacle therein for a quantity of bone graft material.

In one form, the cup-shaped wall has at least a portion that is substantially flat. The discrete receptacle is formed in the substantially flat wall portion.

In one form, the body is made from polyetheretherketone (PEEK).

In one form, the body is made from a non-PEEK material that is one of metal and non-metal.

In one form, the body has an elongate shape with a length between first and second ends and a width. At least a part of the second anchoring part has a cup shape. The stem extends away from the part of the second anchoring portion with the cup shape to the first body end. Another part of the body extends away from the part of the second anchoring portion with the cup shape at a location spaced from a location where the stem extends away from the part of the second anchoring portion with the cup shape.

In one form, the another part of the body extends away from the part of the second anchoring portion with the cup shape in a direction away from the first body end.

In one form, the stem has an elongate shape with a central axis and a flat profile approximated by a reference plane containing the central axis. The second anchoring portion has a cup-shaped wall with a substantially flat surface to bear against the second bone component with the second anchoring portion in its operative position. The flat surface of the cup-shaped wall is angled in two dimensions with respect to the reference plane.

In one form, the second anchoring portion has a surface that has at least a portion with a convex shape to be directed into the cavity in the at least second bone component so as to appose at least a part of a surface on the at least second component bounding the cavity.

In one form, at least a part of the second anchoring portion has a cup-shaped surface with an axis. The convex shape is an arcuate shape extending at least partially around the axis.

In one form, the second anchoring portion has a cup-shaped wall through which an opening is defined to accept the second fastener.

In one form, the second anchoring portion has a cup-shaped wall with a bottom wall portion at which a first connector is provided. The implant is provided in further combination with a first bracing component with a second connector. The first and second connectors are configured to be joinable to releasably maintain the first bracing component in an operative position on the implant.

In one form, the cup-shaped wall has an axis. The first bracing component is elongate with a length. With the first bracing component in its operative position, the length of the first bracing component aligns with the axis of the cup-shaped wall.

In one form, the implant is provided in combination with a cutting tool to be operated to produce the predetermined cavity shape in the at least second bone component. With the second anchoring portion in its operative position, a surface on the at least portion of the second anchoring portion that is extended into the cavity is apposed to at least a part of a surface on the at least second bone component bounding the cavity.

In one form, the cutting tool has a reamer with a shaft that is turned to cause a cutting surface on the reamer to produce the predetermined cavity shape in the at least second component.

In one form, the predetermined cavity shape is a cup shape.

In one form, the stem has a plurality of openings therein each to cooperate with a fastener usable to fix the stem relative to the first bone component. The implant is provided in further combination with an outrigger guide assembly that is releasably attachable to the implant. The outrigger guide assembly has guide openings to facilitate controlled formation of a plurality of openings in the first bone component, each alignable with one of the openings in the stem.

In one form, one of the openings in the stem is elongate.

In one form, the combination described above is provided in further combination with a bracing component. The outrigger guide assembly is configured to facilitate formation of a first of the plurality of openings such that the first bracing component can be directed into the first opening and the one elongate stem opening at one end thereof to allow the implant to shift relative to the first bracing component to thereby reside at an opposite end of the one elongate stem opening.

In one form, the stem has a plurality of openings therein, each to cooperate with a fastener usable to fix the stem relative to the first bone component. One of the openings in the stem is elongate.

In one form, the stem has a plurality of openings therein each to cooperate with a fastener usable to fix the stem relative to the first bone component. The implant is provided in further combination with an outrigger guide assembly that is releasably attachable to the implant and has guide openings to facilitate controlled formation of a plurality of openings in the first bone component, each alignable with one of the openings in the stem.

In one form, the combination described above is provided in further combination with a second bracing component configured to be connected to the first bone component.

In one form, the stem has an elongate opening therein through which the second bracing component can be extended.

In one form, the combination described above is provided in further combination with a tool for engaging the first and second bracing components and urging the first and second bracing components towards each other.

In one form, the invention is directed to a method of fusing bone components. The method includes the steps of: obtaining the implant described above; directing the stem to within the first bone component to place the first anchoring component in its operative position; fixing the stem in its operative position using at least a first fastener; strategically removing bone from at least a second bone component to define a cavity at a placement location for the second anchoring portion; placing the second anchoring portion in its operative position wherein at least a part of the second anchoring portion overlies the at least one bone at the placement location; and fixing the second anchoring portion in its operative position using at least a second fastener.

In one form, the first bone component is a radius bone and the second bone component is a carpal bone.

In one form, the at least second bone component is multiple carpal bones.

In one form, the step of strategically removing bone involves removing bone using a reamer with a rotary cutting surface.

In one form, the method further includes the step of placing bone graft material between the second anchoring portion and bone at the placement location.

In one form, the step of strategically removing bone involves removing bone from the first bone component at another placement location. With the second anchoring portion in its operative position, the second anchoring portion overlies the another placement location.

In one form, the first bone component is a tibia and the at least second bone component is a tarsal bone.

In one form, the first bone component is a metatarsal and the second bone component is a tarsal bone.

In one form, the step of strategically removing bone involves removing bone to define the cavity at the placement location with a shape that is complementary to the part of the second anchoring portion that overlies the placement location.

In one form, the step of strategically removing bone involves removing bone in a manner to allow the part of the second anchoring portion that overlies the placement location to be recessed in the cavity at the placement location.

In one form, the step of using a reamer involves using the reamer so that the rotary cutting surface removes bone simultaneously from a plurality of bone components.

In one form, the cavity at the placement location has a tapered shape. The step of placing the second anchoring portion involves directing a part of the second anchoring portion into the cavity so that at least one bone surface surrounding the cavity cooperates with a part of the second anchoring portion to consistently guide the second anchoring portion into its operative position.

In one form, the second anchoring portion has a cup-shaped wall. The step of fixing the second anchoring portion involves directing a plurality of fasteners through the cup-shaped wall into different bone components.

In one form, at least two of the plurality of fasteners are directed into different bone components at different angles.

In one form, the second anchoring portion has a discrete cutout therein. The method further includes the step of fixing the second anchoring portion in its operative position with the cutout located to avoid impingement of a radial ulnar joint by the implant.

In one form, the method further includes the steps of: connecting a first bracing component to the implant; directing a second bracing component through an elongate opening in the first anchoring portion and into the first bone component; and exerting a force tending to draw the first and second anchoring portions towards each other, whereby the second bracing component moves within the elongate opening and the first bone component and at least second bone component are urged towards each other into a desired relationship.

In one form, the step of fixing the stem in its operative position involves directing the first fastener into the first bone component and stem after the first bone component and at least second bone component are placed in the desired relationship.

In one form, the method further includes the step of broaching the first bone component with a broaching tool and after broaching the first bone component, separating the broaching tool from the first bone component and directing the stem to within the first bone component.

In one form, the rotary cutting surface is configured to produce a cup-shaped cavity and has a pilot extension.

In one form, the method further includes the step of forming a pilot bore in the at least second bone component.

In one form, the method further includes the step of releasably connecting a guide to the second anchoring portion. The step of placing the second anchoring portion in its operative position involves directing a part of the guide into the pilot bore to consistently guide the second anchoring portion into its operative position.

In one form, the method further includes the step of provisionally securing the second anchoring part in its operative position with temporary fasteners before using the at least first fastener.

In one form, the method further includes the step of stabilizing the first bone component and the second bone component before strategically removing bone from the at least second bone component.

In one form, the method further involves the step of using the broaching tool as a guide to form a pilot bore in the at least second bone component.

In one form, with the second anchoring portion in its operative position, a surface on the second anchoring portion is situated so as to appose a surface bounding the cavity.

BRIEF DESCRIPTION OF THE DRAWINGS

FIG. 1 is a schematic representation of an implant for fusing separate bone components, according to the invention;

FIG. 2 is a schematic representation showing additional details of a body on the implant in FIG. 1;

FIG. 3 is a schematic representation showing additional details of the body in FIGS. 1 and 2 and an optional additional implant body part;

FIG. 4 is a side elevation view of a specific, exemplary form of implant, as shown schematically in FIGS. 1-3;

FIG. 5 is a perspective view of the implant in FIG. 4;

FIG. 18 is a view as in FIG. 13 and showing K-wires inserted to stabilize bones in the wrist region;

FIG. 19 corresponds to FIG. 18 from a different perspective;

DETAILED DESCRIPTION OF THE PREFERRED EMBODIMENTS

Figure 6:
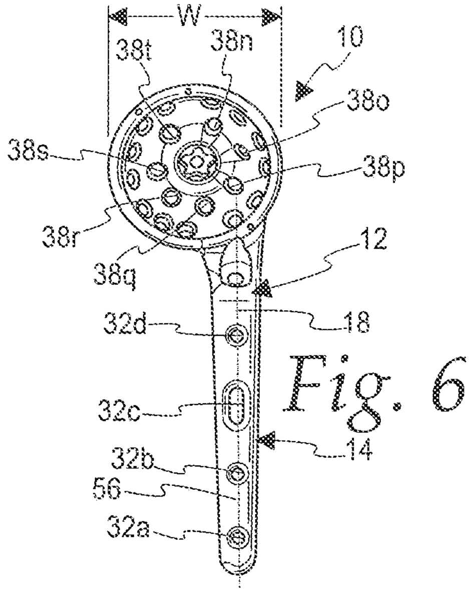
FIG. 6 is a plan view of the implant in FIGS. 4 and 5.

Referring initially to FIG. 1, a preferred form of implant for fusing at least two bones/bone components, according to the invention, is shown at 10. The implant 10 consists of a body 12 with first and second anchoring portions 14, 16, respectively. The first anchoring portion 14 has a stem 18 configured to be directed to within a first bone component to place the first anchoring portion 14 in an operative position. The first anchoring portion 14 is further configured to cooperate with at least a first fastener 20 usable to cause the stem 18 to be fixed relative to the first bone component and thereby maintain the first anchoring portion 14 in its operative position.

The second anchoring portion 16 is configured to overlie at least a second bone component with the second anchoring portion 16 in an operative position and is further configured to cooperate with at least a second fastener 20 usable to fix a part of the second anchoring portion to the second bone component to thereby maintain the second anchoring portion 16 in its operative position.

The fasteners 20 for the first and second anchoring portions 14, 16 may be the same or different and may take any known form.

The body 12 may be made in multiple pieces but in a preferred form has a single rigid piece that defines the first and second anchoring portions 14, 16.

As shown in FIG. 2, the body 12 has a length between first and second ends 22, 24, respectively. The stem 18, in one preferred form, extends fully to the first body end 22.

In FIG. 3, the body 12, consisting of the first and second anchoring portions 14, 16, is shown in more detail and with an optional modification. In this general form, the second anchoring portion 16 has a cup-shaped part 26 from which a body part 28 extends. The body part 28 and first anchoring portion 14 typically project from different locations on the cup-shaped part 26. With the FIG. 3 construction, the second anchoring portion 16 may by itself extend fully to the second body end 24. Alternatively, the body part 28 may extend either up to an end of the cup-shaped part 26 and to the second body end 24 or therebeyond as to by itself define the second body end 24.

It should be understood that multiple cup-shaped parts 26 could be incorporated into the body 12.

The schematic showing of the components in FIGS. 1-3 is intended to encompass the components as shown in specific forms hereinbelow, as well as virtually an unlimited number of variations in those components and their cooperation.

Referring now to FIGS. 4-9, a specific form of the implant 10 will be described. The implant 10 has the aforementioned body 12 with a length L between the first and second ends 22, 24, respectively, and a predominant width W.

The first anchoring portion 14 defines the stem 18 configured to be directed into at least a first bone component 30. The stem 18 is elongate in shape and has a plurality of lengthwise spaced openings 32*a*, 32*b*, 32*c*, 32*d*, each to accept a fastener 20 usable to fix the stem 18 in an operative position relative to the bone component 30. The opening 32*c* is elongate to allow the stem 18 to shift lengthwise relative to a fastener 20 directed therethrough into the first bone component 30.

The second anchoring portion 16 is configured to overlie at least a second bone component 34 and has a cup-shaped wall 36, corresponding to the aforementioned cup-shaped part 26, with a plurality of openings 38*a*-38*t*, each to receive a fastener 20 usable to fix a part of the second anchoring portion 16 directly to at least one of the second bone components 34 with the second anchoring portion 16 in an operative position.

As noted above, the nature of the particular fasteners 20 is not critical to the present invention. Typically, threaded fasteners 20 will be directed through or into the openings 32, 38 and will purchase bone to effect fixation.

As noted above, in reference to FIG. 3, the second anchoring portion 16 has a generically depicted cup-shaped part 26, that may have a wide range of different shapes. The corresponding cup-shaped wall 36 may be symmetrical around a central axis 40, as depicted for the cup-shaped wall in FIGS. 4-9, or may have a non-symmetrical shape.

As depicted, the cup-shaped wall 36 has a cup-shaped concave surface 42 and an oppositely facing cup-shaped convex surface 44. As depicted, the surfaces 42, 44 are complementary in shape, with the wall 36 having a uniform thickness therebetween. This, however, is not a requirement as the shapes of the surfaces 42, 44 could be considerably different.

At least a part of the second anchoring portion 16 has this cup shape. As depicted, the cup-shaped wall 36 makes up substantially the entirety of the second anchoring portion 16.

In the depicted form, the convex surface 44 extends around the axis 40 and has an axial width AW tapering between a top rim 46 and a flat bottom wall portion 48. The bottom wall portion actually has a “W” shape, as seen in cross-section in FIG. 9, but is effectively flat, and will be considered such since the downwardly facing surface 50 thereon will seat stably against a flat bone surface.

Figure 9:
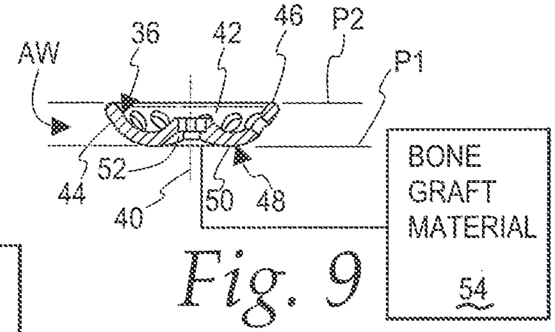
FIG. 9 is a cross-sectional view of the implant taken along line 9-9 of FIG. 8.

The surface 44 is convex from two different perspectives—in cross-section as in FIG. 9 and as viewed from an axial perspective.

The "W" shape forms a discrete receptacle 52 in the bottom wall portion 48 to receive bone graft material 54.

The convex surface 44 is configured to appose a surface on at least one of the second bone components 34 with the second anchoring portion 16 in its operative position. Bone graft material 54 is in contact with the cup-shaped wall 36 over the surface bounding the receptacle 52 and the bone region which the bottom wall portion 48 overlies. The bottom wall surface 50 may bear against at least one of the second bone components 34 but may be spaced above the same to accommodate an appropriate volume of bone graft material 54. Bone graft material 54 is not required or may be located other than at the bottom wall portion 48, which may allow the bottom wall portion 48 to directly contact at least one of the second bone components 34.

The receptacle 52 may take many different forms. Further, multiple receptacles might be formed at different locations.

In the form depicted, the first anchoring portion 14 is elongate and has a lengthwise center line 56. The center line 56 is offset from the central axis 40 of the cup-shaped wall 36, as seen most clearly in FIG. 6.

In the event that the body part 28 is provided, it preferably extends away from the cup-shaped wall 36 at a location spaced circumferentially from a location at 58 where the first anchoring part 14 projects away from the cup-shaped wall 36.

In most constructions, the body part 28 projects away from the cup-shaped wall 36 in a direction away from the first end 22 of the body 12. As noted above, the body part 28 may extend fully to the second body end 24. The cup-shaped part 26 may likewise extend fully to the second body end 24, or may be adjacent to or spaced therefrom.

In one modified form, an optional, discrete cutout 59 is formed through the rim 46, as shown in dotted lines in FIG. 5, to avoid interference at certain joint sites, as explained hereinbelow.

The stem 18 has an obround shape as viewed in cross-section orthogonally to the length of the stem 18. Other cross-sectional shapes are contemplated, such as rectilinear, elliptical, etc. The width of the stem 18 along the major axis of the obround cross-sectional shape increases from the first body end 22 up to the cup-shaped wall 36.

The body 12 may be made from any of a number of different materials. In one form, it is made from metal.

Figure 10:
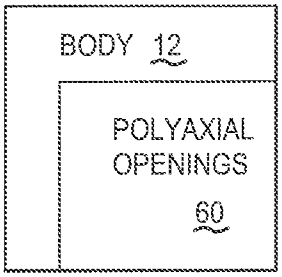
FIG. 10 is a schematic representation of polyaxial openings in a body, as on the implant in FIGS. 1-9.

In a more preferred form, the body 12 is made from a non-metal material such as polyetheretherketone (PEEK), or other medical grade plastic. The use of PEEK material facilitates the formation of polyaxial openings, as identified generically at 60 in FIG. 10, at each location on the body 12 where it is desirable to be able to direct the fasteners 20 at different angles threadably through each such opening 60.

Figure 11:
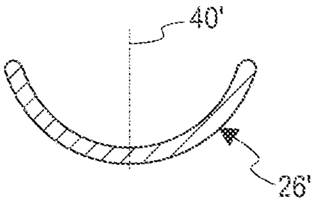
FIG. 11 is a cross-sectional representation of an alternative form of a cup-shaped part, as shown on the implant in FIGS. 4-9.

As noted above, the particular "cup shape" for the cup-shaped part 26 of the second anchoring portion 16 may vary considerably. As shown in FIG. 11, the cup-shaped part 26' is formed as a hollowed segment of a sphere, which has a central axis 40'.

Figure 12:
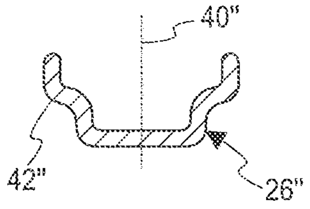
FIG. 12 is a view as in FIG. 11 showing a further alternative form.

In FIG. 12, a variation is shown wherein the cup-shaped part 26" has a convex surface 42" made up of portions with radii of different lengths as viewed orthogonally to the axis 40".

These are just examples of the multitude of different forms that the cup-shaped part 26, making up at least part of the second anchoring portion 16, may take, keeping in mind that symmetry is not required around a respective axis 40 and the cup-shaped wall 36 need not have a uniform thickness.

A method of fusing bone components is described in FIGS. 13-36 on a human wrist. This is but one exemplary application of the implant, described above.

The wrist is exposed and the arthritic joint surfaces are decorticated and residual cartilage removed. The distal end of the radius 64 is exposed and a drill placed into the central intramedullary canal to determine the longitudinal axis of the radius.

Figure 13:
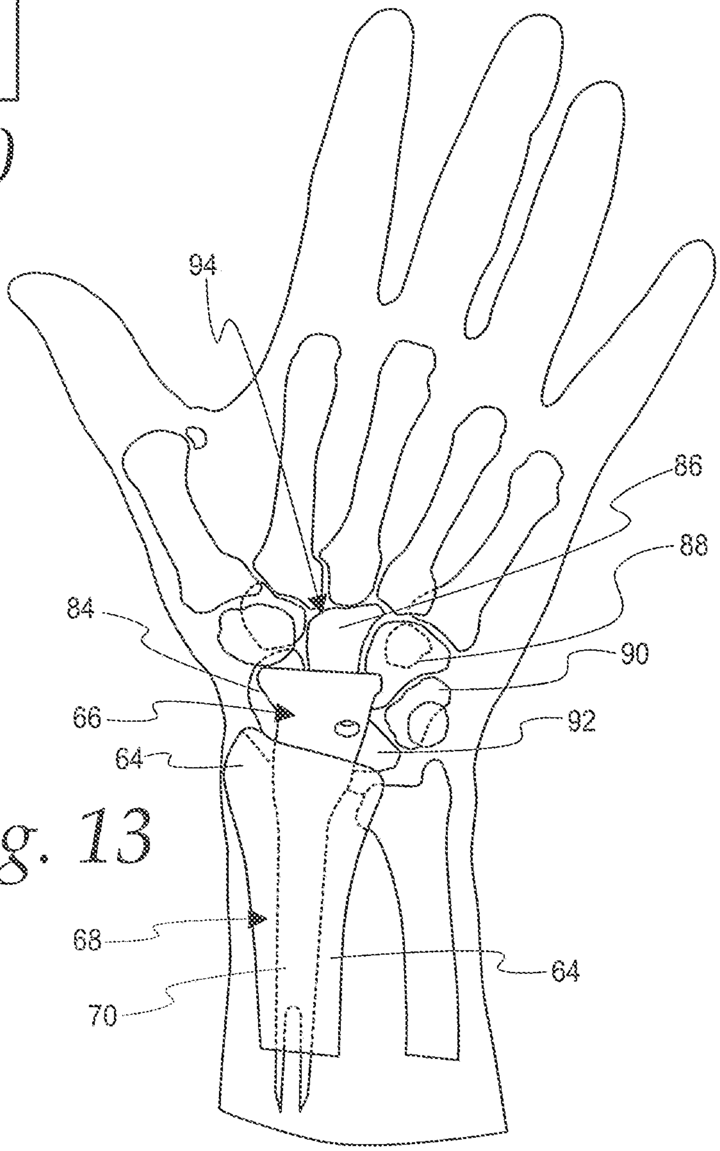
FIG. 13 is a depiction of a human hand and forearm region at which a wrist fusion is to be performed and with a broaching tool inserted into an intramedullary canal on the radius.
Figure 14:
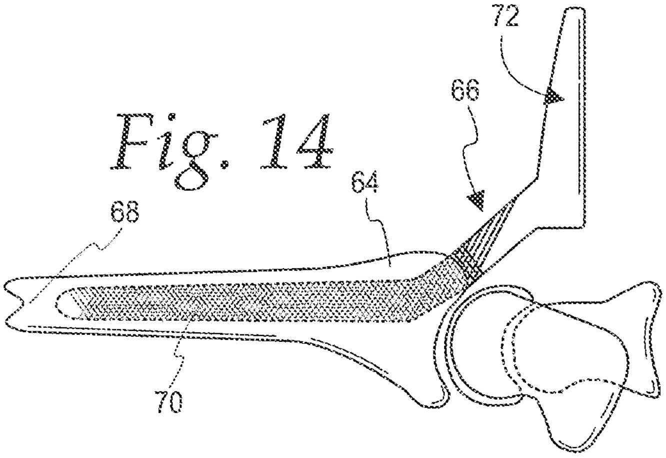
FIG. 14 corresponds to FIG. 13 from a different perspective.
Figure 15:
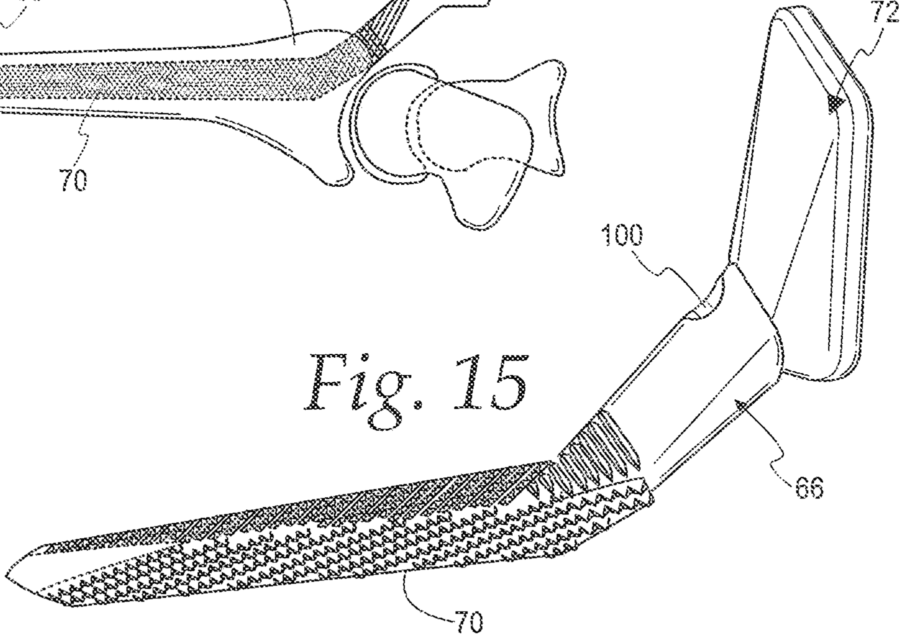
FIG. 15 is a perspective view of the broaching tool depicted in FIGS. 13 and 14.

As seen in FIGS. 13-15, a broaching tool 66 is used to prepare the radius canal 68, and inserted from the articular end of the radius 64 centrally into the canal 68. The penetrating portion 70 of the broaching tool 66 preferably matches the contour of the stem 18. In the depicted form, a handle 72 on the broaching tool is offset so that when the broaching tool 66 is fully seated as in FIGS. 13 and 14, reduction of the joint surface is permitted.

Figure 16:
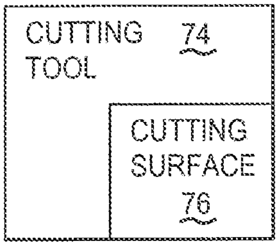
FIG. 16 is a schematic representation of a cutting tool usable to form a cavity to receive a portion of the inventive implant.

While not required, one preferred method of using the implant 10 is carried out with the assistance of a cutting tool, as shown generically at 74 in FIG. 16.

The cutting tool 74 has at least one cutting surface 76 configured so that as the cutting tool 74 is operated, it is capable of producing a cavity with a predetermined shape. The cutting tool 74 is not limited in terms of its configuration or manner of operation so long as it is capable of consistently producing a cavity with a predetermined shape.

Figure 17:
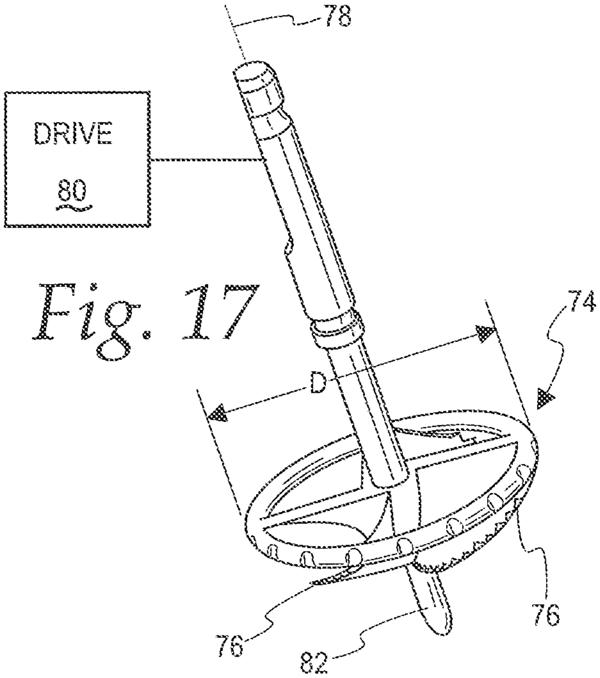
FIG. 17 is a perspective view of an exemplary form of cutting tool as shown schematically in FIG. 16.

In an exemplary form, as shown in FIG. 17, the cutting tool 74 is in the form of a reamer with a plurality of cutting surfaces 76. The reamer 74 is turned around an axis 78 through an appropriate drive 80, as an incident of which the cutting surfaces 76 are capable of progressively removing bone in a symmetrical pattern around the axis 78.

The depicted cutting surfaces 76 are configured to produce a cup-shaped cavity. The reamer 74 has a pilot extension 82 projecting axially beyond the cutting surfaces 76.

The cutting tool/reamer 74 has a footprint diameter D selected based upon the particular implant configuration and the desired number of bone components to be fused. In the particular wrist application depicted, the implant 10 is configured and dimensioned to allow fusion of five carpal bones—the scaphoid 84, capitate 86, hamate 88, triquetrum 90, and lunate 92—to each other and the radius 64.

Preparatory to using the reamer 74, and with the broaching tool in place, as in FIGS. 13, 14, 18, and 19, the carpus at 94, consisting of, inter alia, the scaphoid 84, capitate 86, hamate 88, triquetrum 90, and lunate 92, is stabilized relative to the radius 64 as by using conventional K-wires 96 directed through bones in the carpus 94 and into the radius 64. This assures that the wrist is fused in the preferred angle of dorsiflexion.

Once the region is stabilized, a pilot bore 98 is formed in the carpus 94. The broaching tool 66 has a guide opening 100 for a boring tool 102 that is directed towards a target location in the region whereat the second anchoring portion 16 is placed in its operative position. The boring tool 102 may be manually controlled or may be turned through an appropriate drive 104.

Figure 20:
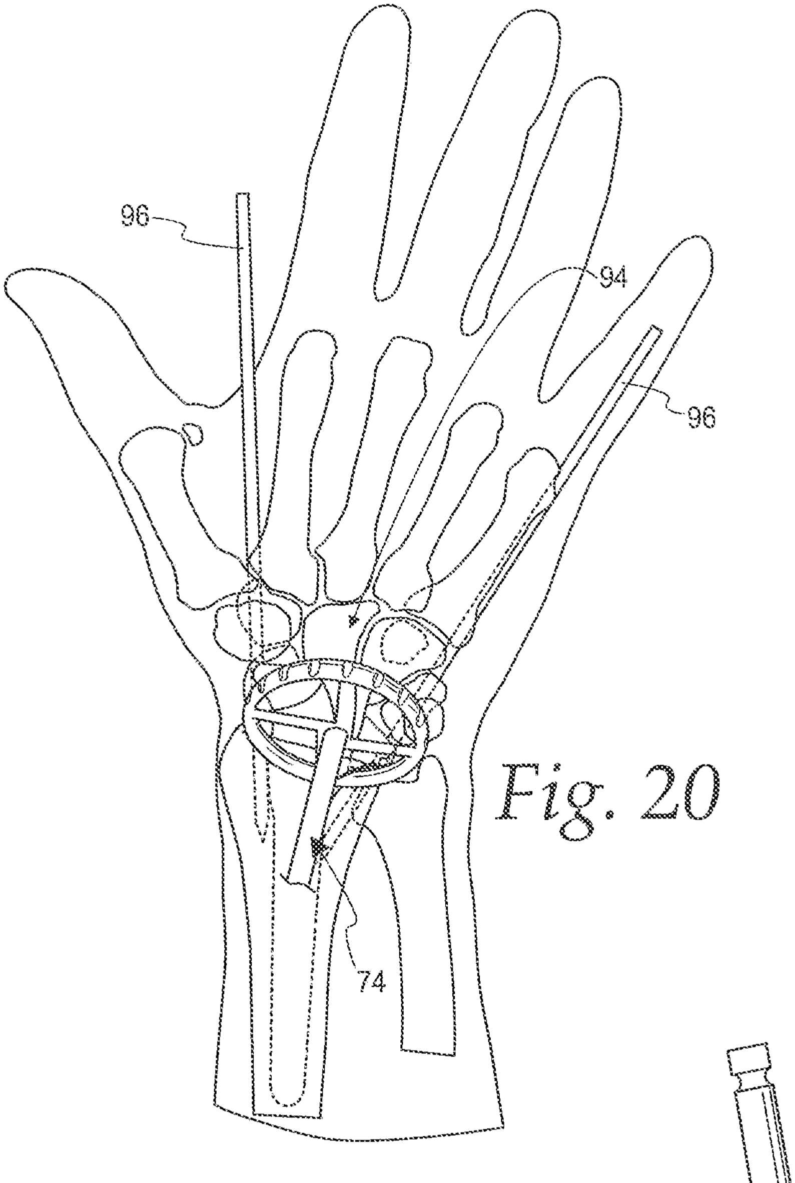
FIG. 20 is a view as in FIG. 18 wherein the cutting tool is operated to create a cavity for receiving a portion of the inventive implant.
Figure 21:
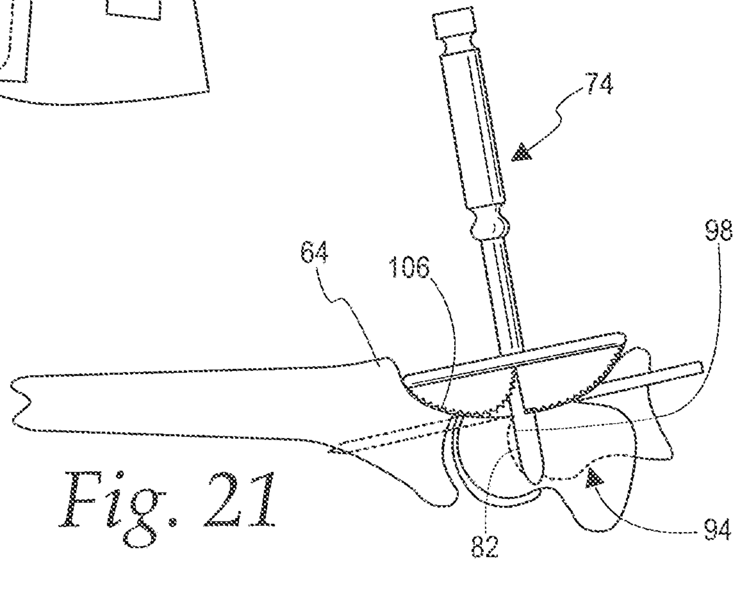
FIG. 21 corresponds to FIG. 20 from a different perspective.

As shown in FIGS. 20 and 21, with a region of the carpus 94 stabilized by the K-wires 96, the broaching tool 66 is removed and the cutting tool/reamer 74 placed strategically over the carpus region and the distal end of the radius 64 by directing the pilot extension 82 thereon into the pilot bore 98.

By operating the cutting tool/reamer 74, a desired quantity of surface cortical bone can be removed to create a cavity 106 in at least the carpus 94, and as depicted in the radius 64.

The overall cup-shaped cavity 106 is complementary in shape to the second anchoring portion and, more particularly, the concave surface 42 as well as potentially the surface 50 on the bottom wall portion 48.

The cutting path for the cutting tool/reamer 74 is dictated by the particular fusion that is desired. It is not necessary that the surface cortical bone be removed from the radius 64 to use the implant 10. The diameter D, which represents the effective cutting diameter of the cutting surfaces 76, also determines the number of carpal bones to be treated as well as the particular area of the placement locations thereon. The reamer/cutting tool 74 can be simply and conveniently operated to strategically and precisely remove cortical bone surface to provide a bed for effective fusion.

Figure 22:
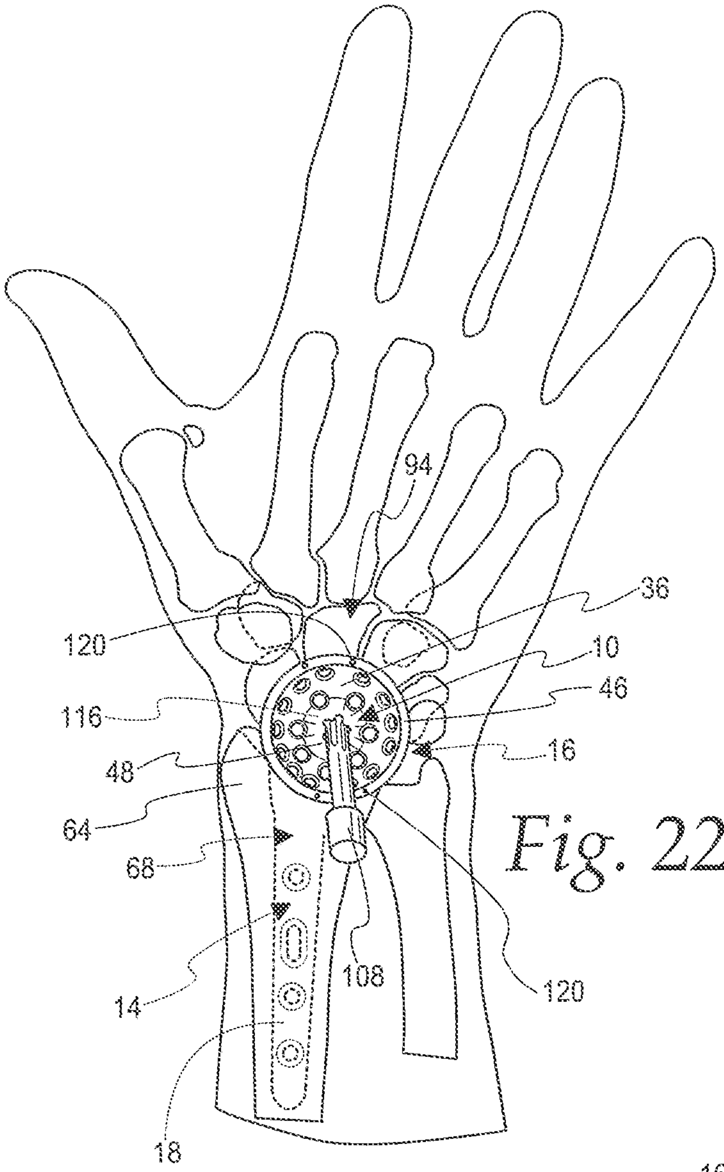
FIG. 22 is a view as in FIG. 20 wherein the cutting tool and K-wires have been removed and the inventive implant has been placed in an operative position and provisionally held in place through K-wires.
Figure 23:
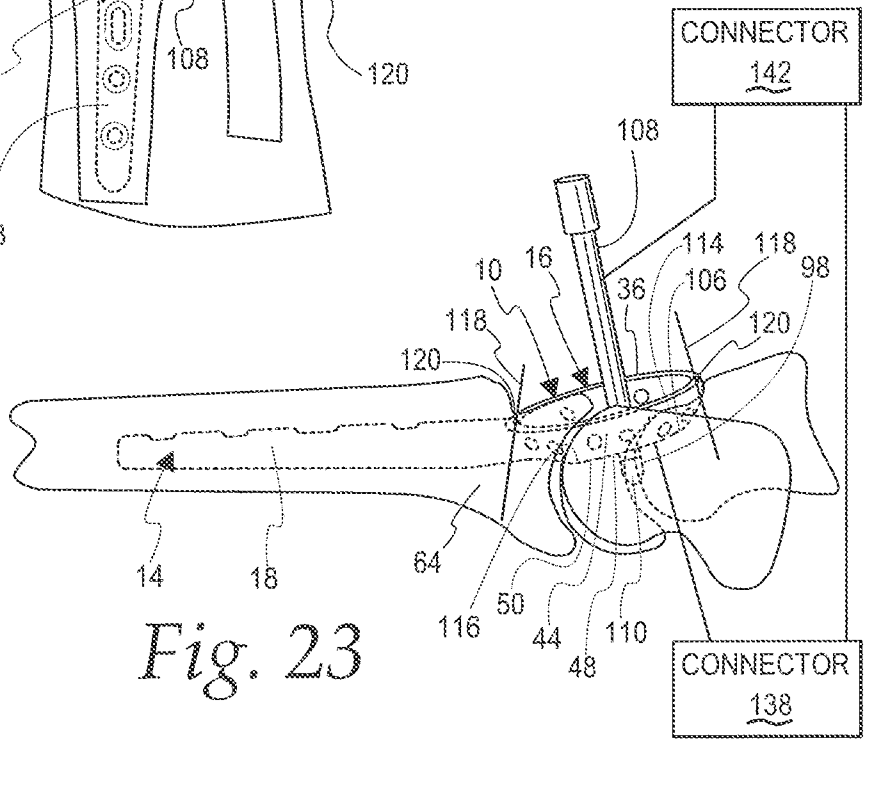
FIG. 23 corresponds to FIG. 22 but from a different perspective.

As seen in FIGS. 22 and 23, once the bone treatment with the cutting tool/reamer 74 is completed, bone graft material can be applied within the receptacle 52 on the cup-shaped wall 36. The stem 18 is inserted into the radius canal 68, whereupon the cup-shaped wall 36 is pressed into the cavity 106.

A guide/inserter bar 108 can be releasably connected to the bottom wall portion 48 and may have a leading part 110 that projects past the bottom wall portion 48 to advance into the pilot bore 98. The guide 108 is graspable to facilitate reorientation of the cup-shaped wall 36 with the leading portion 110 facilitating alignment of the convex surface 44 with the complementary surface 114 bounding the cavity 106, as defined cooperatively by the carpus 94 and radius 64.

In FIGS. 22 and 23, the first and second anchoring portions 14, 16, respectively, are shown in their respective operative positions wherein the convex surface 44 is apposed to the surface 114 bounding the cavity 106. The surface 50 on the bottom wall portion 48 may likewise appose the bottom surface region 116 bounding the cavity 106.

With the first and second anchoring portions 14, 16 in their respective operative positions, provisional fixation of the implant 10 can be effected using small K-wires 118, directed in this case through openings 120 through the rim 46 of the cup-shaped wall 36 and into the carpus 94 and radius 64.

Figure 24:
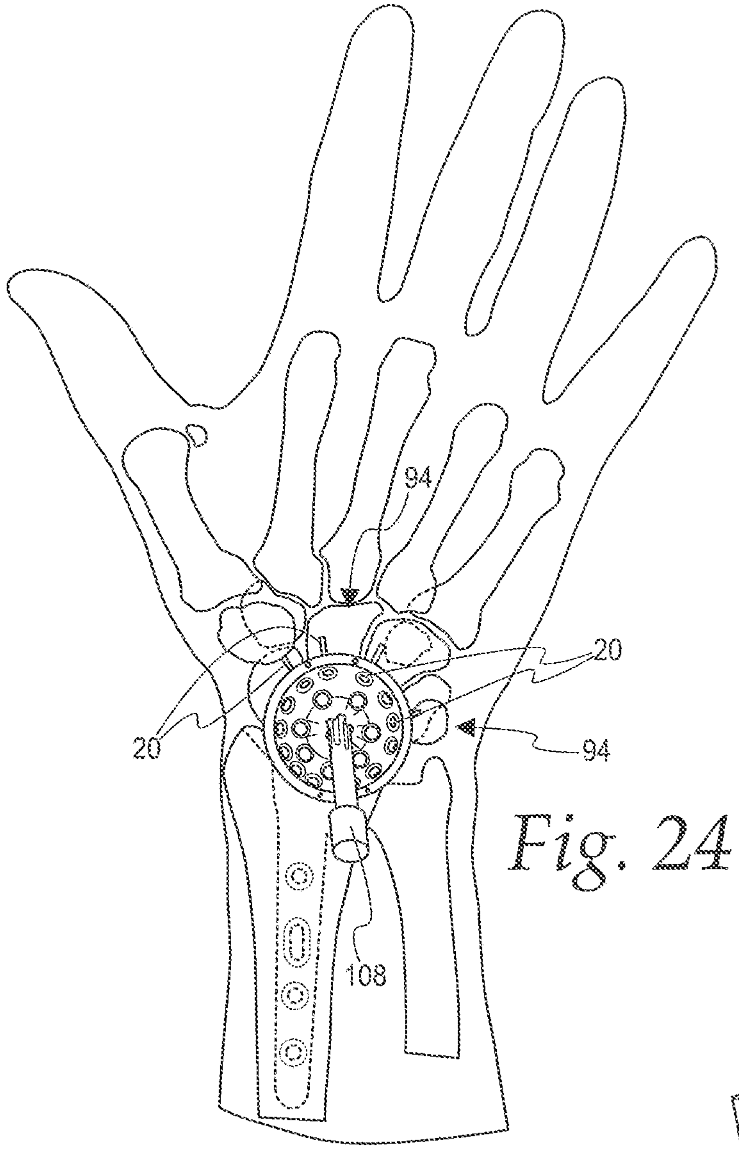
FIG. 24 is a view as in FIG. 22 wherein fasteners have been directed through one portion of the implant.
Figure 25:
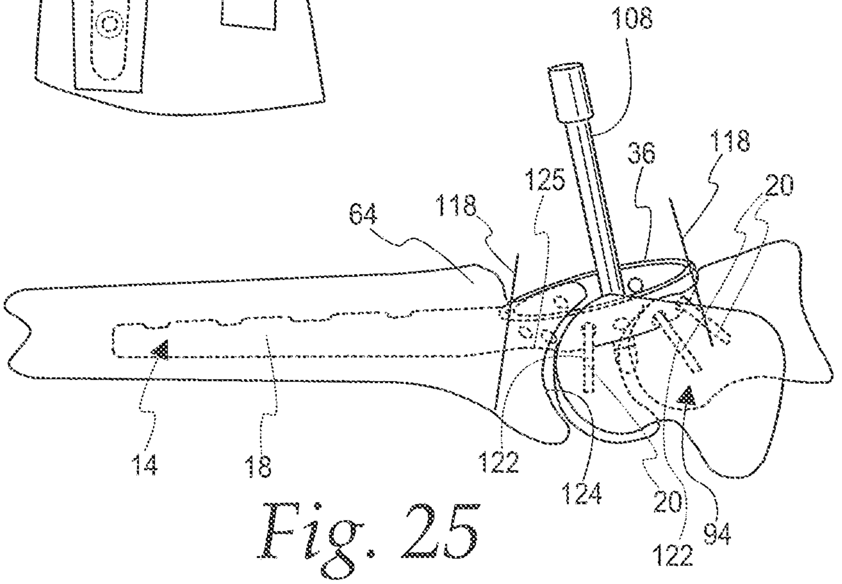
FIG. 25 corresponds to FIG. 24 but from a different perspective.
Figure 27:
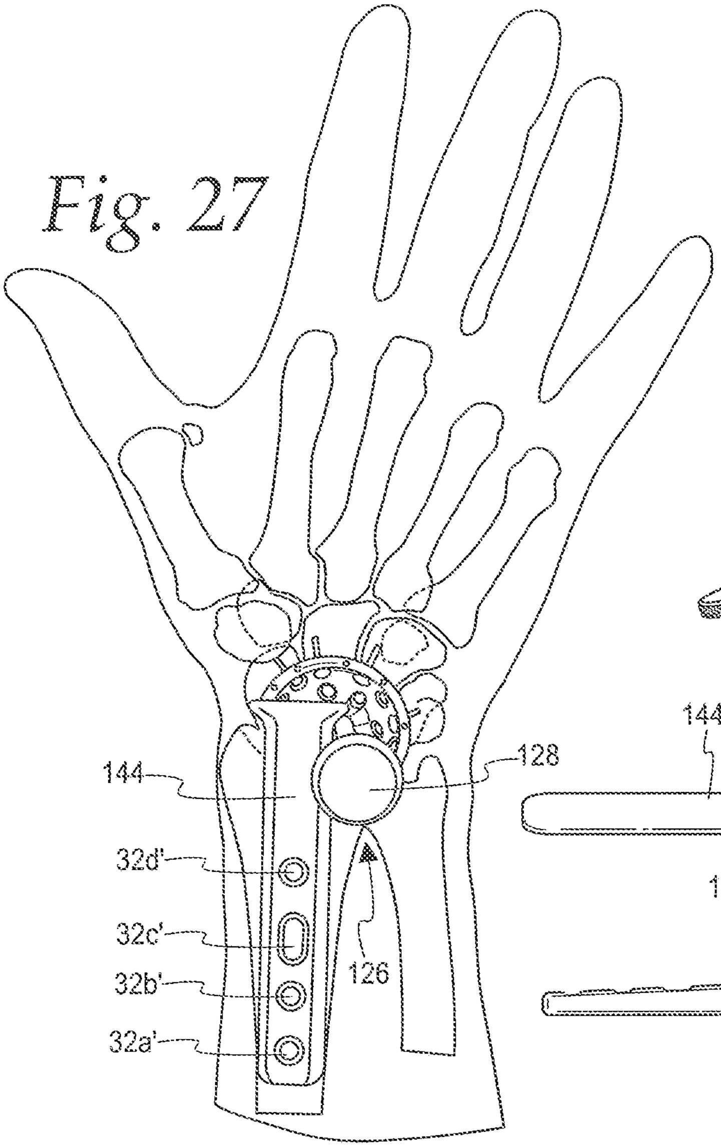
FIG. 27 is a view as in FIG. 24 wherein the outrigger guide assembly of FIG. 26 has been placed in an operative position.
Figure 26:
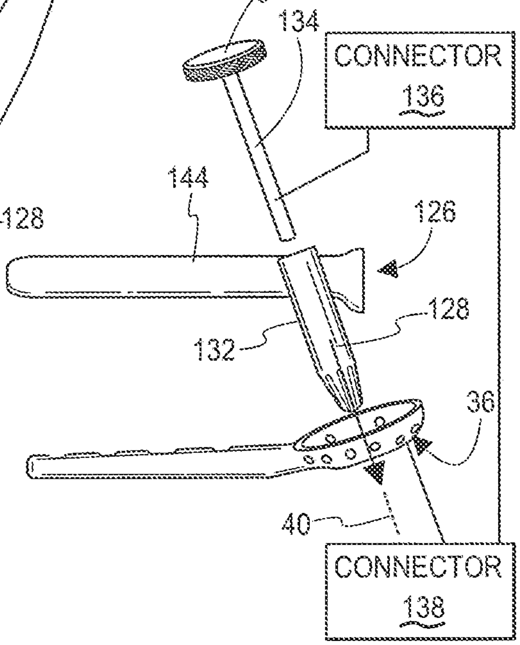
FIG. 26 is an exploded view of an outrigger guide assembly in relationship to the inventive implant.

As shown in FIGS. 24 and 25, with the implant 10 provisionally fixed as in FIGS. 22 and 23, holes 122 can be formed strategically into bones of the carpus 94 to accept fasteners 20 directed through openings 38 in the cup-shaped wall 36.

Once the fasteners 20 are secured as in FIGS. 24 and 25, the guide/inserter bar 108 is separated from the cup-shaped wall 36.

While different arrangements of fasteners are contemplated, the fasteners 20 of an appropriate size are directed into each of the scaphoid 84, capitate 86, hamate 88, triquetrum 90, and lunate 92, which collectively define one placement location that the cup-shaped wall 36 overlies.

In this embodiment, cortical bone from the dorsal rim 124 of the radius 64 is also removed so that the cup-shaped wall 36 seats at a second placement location 125 where the cup-shaped wall 36 overlies the radius 64 which, while not required, in this embodiment is reconfigured through the cutting tool/reamer 74. As depicted in FIG. 25, one of the temporary K-wires 118 is directed into the radius 64.

As seen in FIGS. 26-30, an outrigger guide assembly 126 may then be utilized, consisting of a first bracing component 128 releasably connected to the cup-shaped wall 36, and a second bracing component 130. Alternatively, the guide assembly 126 may be attached to any other site on the implant body 12. The aforementioned guide 108 and first bracing component 128, while shown to be different, may be one and the same. The first bracing component 128 consists of an elongate sleeve 132 with a length alignable with the axis 40 of the cup-shaped wall 36. An anchoring part 134 has a connector 136 that is releasably engageable with a connector 138 on the cup-shaped wall 36. The connectors 136, 138 may make threaded engagement or may be otherwise configured. With the threaded arrangement, utilizing an enlarged head 140 for manual gripping, the anchoring part 134 may be turned to engage and release the connectors 136 138. With the connectors 136, 138 engaged, the sleeve 132 and anchoring part 134 are fixed with their lengths aligned with the axis 40.

It should be noted that the connector 138 is also usable to releasably engage a connector 142 on the aforementioned guide/inserter bar 108, as shown schematically in FIG. 23, to make a releasable connection therewith.

Figure 28:
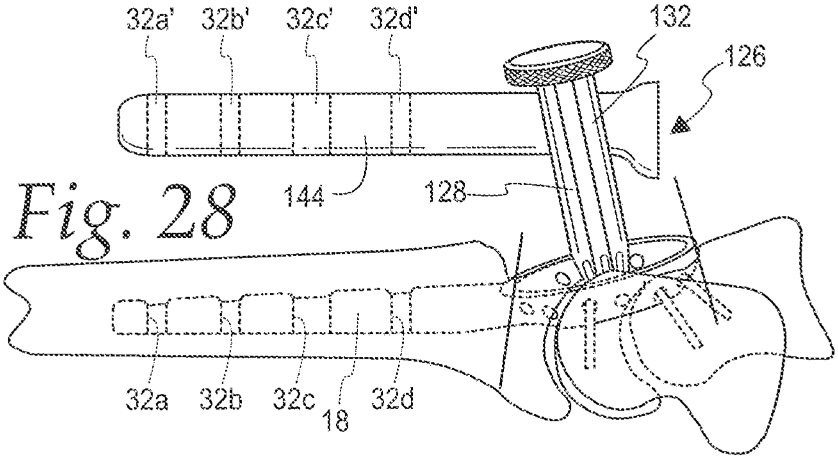
FIG. 28 corresponds to FIG. 27 but from a different perspective.
Figure 29:
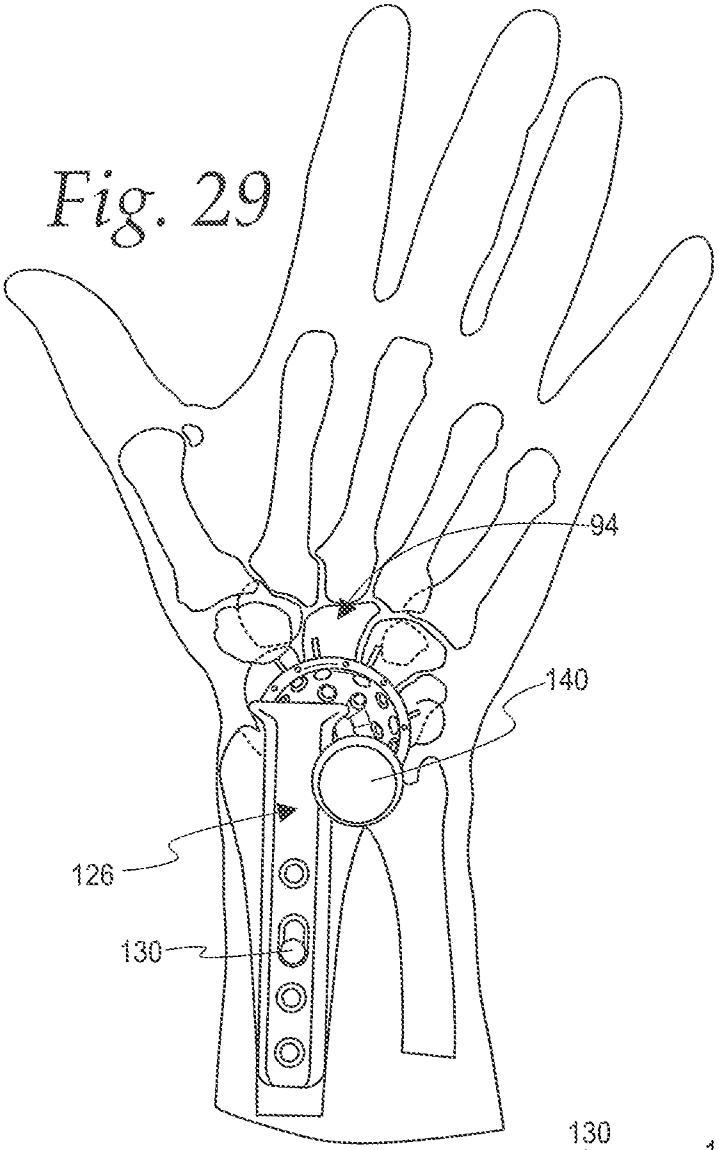
FIG. 29 is a view as in FIG. 27 with the addition of an anchoring part directed into one of the bone components.
Figure 30:
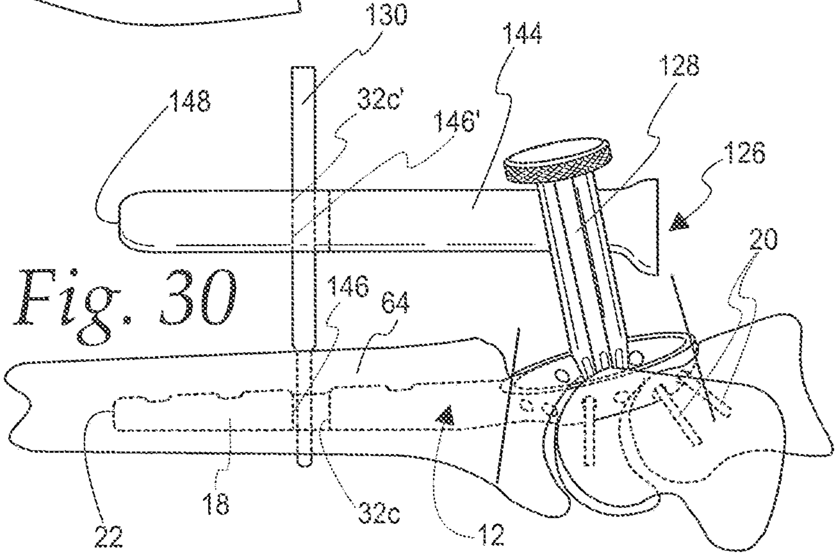
FIG. 30 corresponds to FIG. 30 but from a different perspective.

The sleeve 132 is fixed with respect to an elongate guide bar 144 which has openings **32*a*', 32*b*', 32*c*', 32*d*', corresponding to the stem openings 32*a*, 32*b*, 32*c*, 32*d* in shape and location, whereby with the elongate guide 144 overlying the stem 18 with these components in lengthwise alignment, the openings 32*a*', 32*b*', 32*c*', 32*d*' register with the openings 32*a*, 32*b*, 32*c*, 32*d*, as shown most clearly in FIG. 28**.

The second bracing component 130 is then directed through the opening **32*c*' into the radius 64 and through the stem opening 32*c*. The second bracing component 130 is configured to be slidable within each of the slots 32*c*, 32*c*' lengthwise of the elongate guide 144 and stem 18. The second bracing component 130 is directed into the openings 32*c*', 32*c* to reside at or adjacent an edge 146, 146' closest to the end 22 of the body 12 and the end 148 of the elongate guide 144**.

Figure 31:
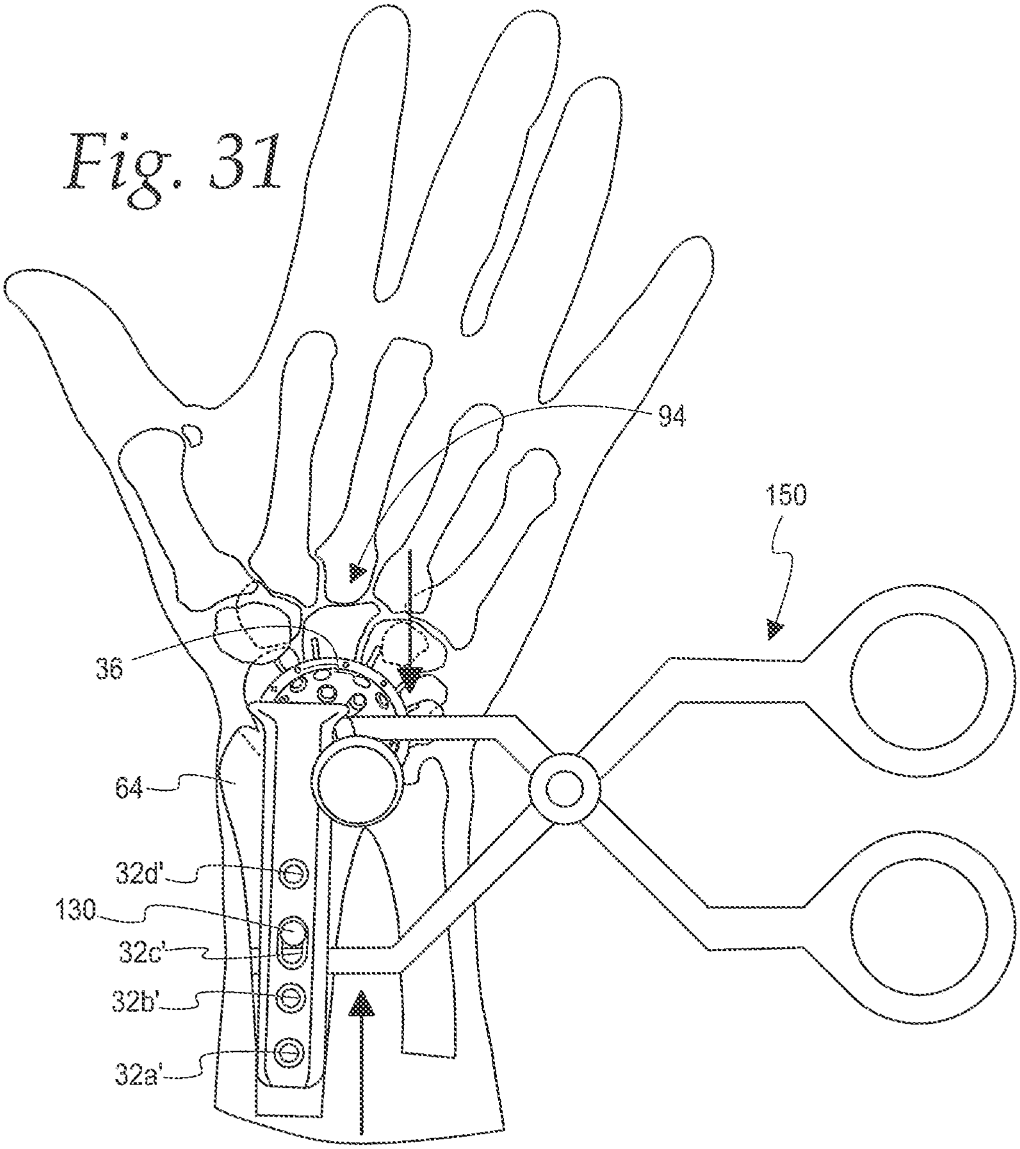
FIG. 31 is a view corresponding to FIG. 29 wherein parts of the outrigger guide assembly are urged towards each other to move bone components to be fused into a desired relationship.
Figure 32:
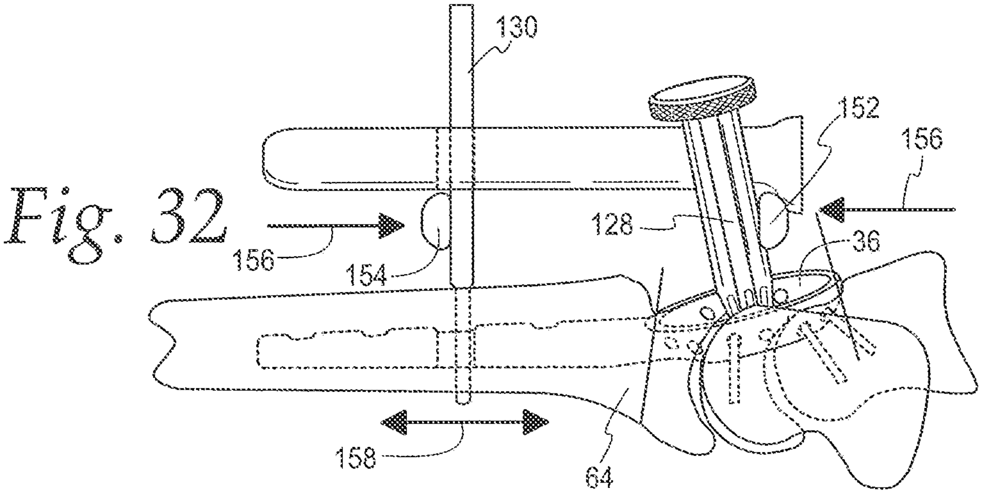
FIG. 32 corresponds to FIG. 31 but from a different perspective.

As shown in FIGS. 31 and 32, a clamping tool 150 is employed with jaws 152, 154 that can be respectively borne against the first and second bracing components 128, 130, respectively, to draw the bracing components 128, 130 towards each other as indicated by the arrows 156. This is permitted by the elongate configuration of the openings **32*c*, 32*c*'. As this occurs, the carpus bone components fixed to the cup-shaped wall 36 are drawn towards the radius 64 along the line of the double-headed arrow 158 into a desired relationship wherein at least one of the engaged carpus bones is compressed against the distal end of the radius 64. While a scissors-type clamping tool 150** is depicted, any type of device or devices might be utilized to effect this compressive movement at the fusion site.

Figure 33:
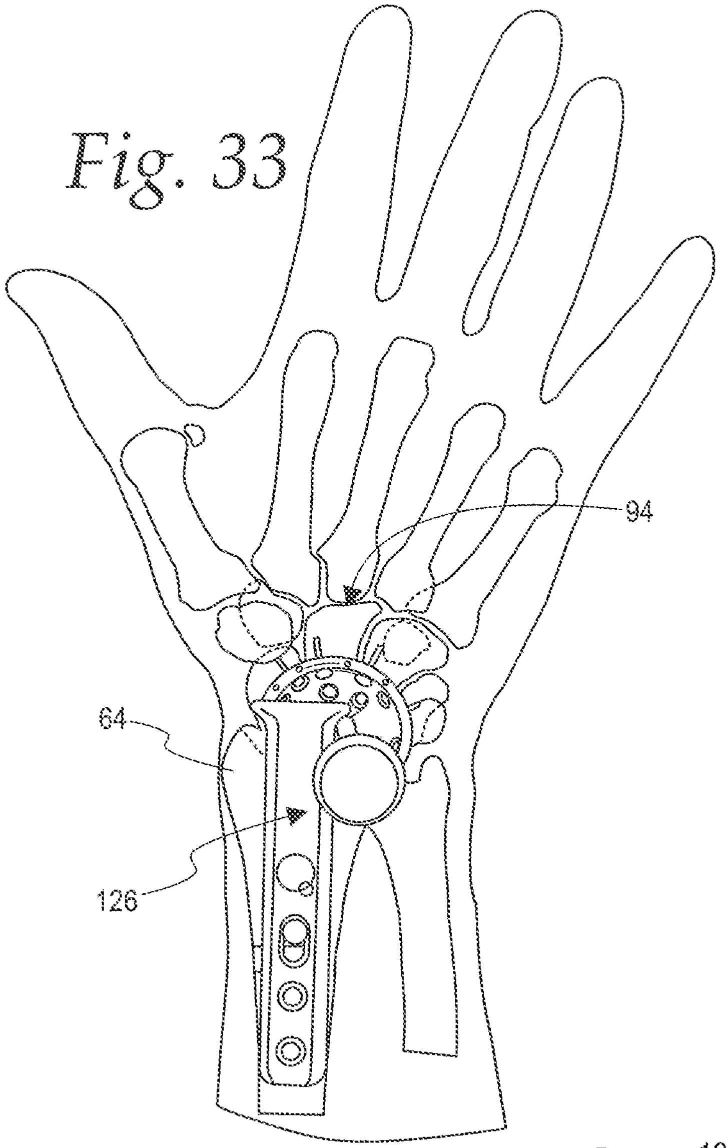
FIG. 33 is a view as in FIG. 31 wherein additional fasteners have been used to maintain the desired relationship of the fused bone components.
Figure 34:
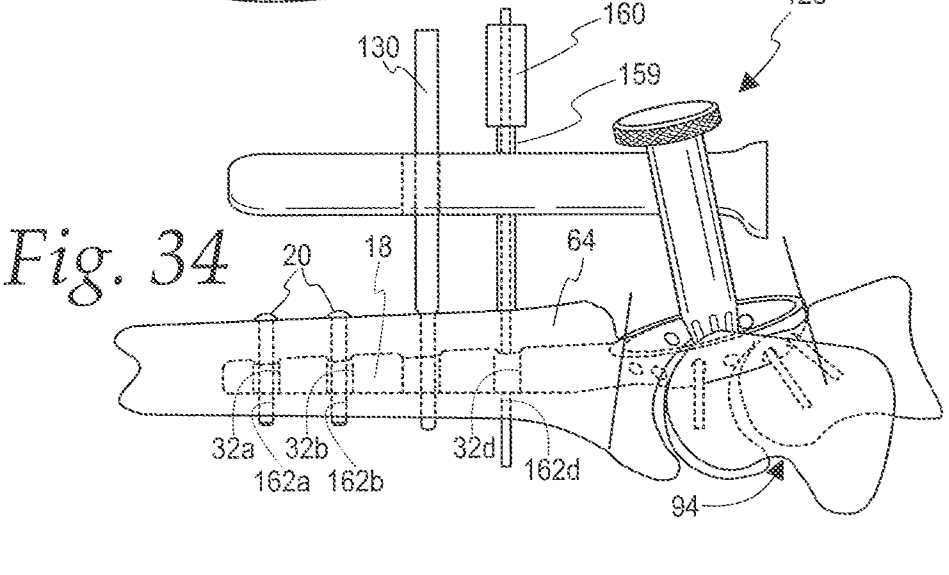
FIG. 34 corresponds to FIG. 33 but from a different perspective.

As shown in FIGS. 33 and 34, once the desired relationship is established between the carpal bones and the radius 64, a drill 159 can be placed through the drill sleeve 160 and used to form openings **162*a*, 162*b*, 162*d* through the radius 64 that register with the openings 32*a*, 32*b*, 32*d* in the stem 18, whereupon fasteners 20 can be utilized to fix the stem 18 relative to the radius 64**.

Figure 35:
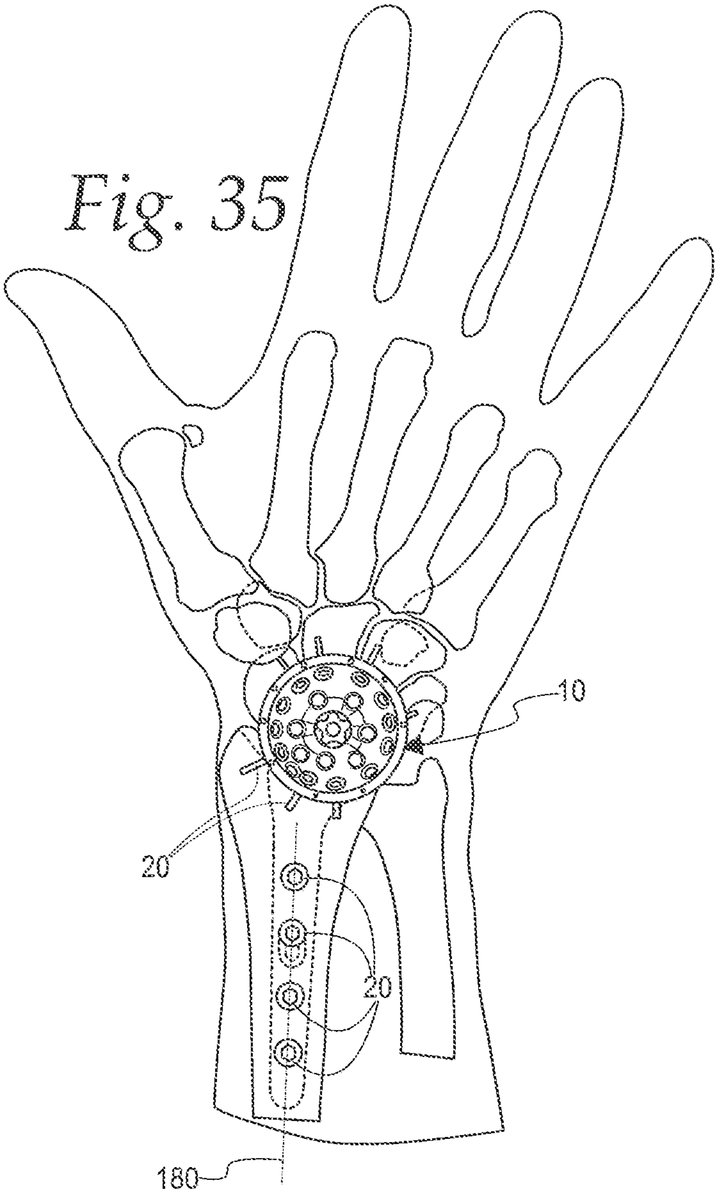
FIG. 35 is a view as in FIG. 33 with the outrigger guide assembly removed.
Figure 36:
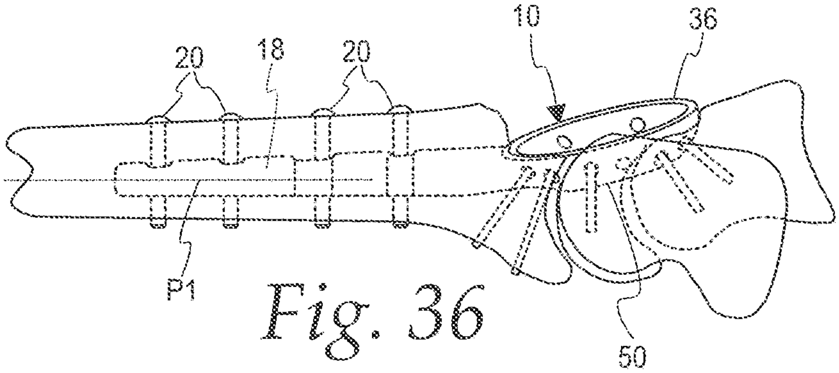
FIG. 36 corresponds to FIG. 35 but from a different perspective.

In FIGS. 35 and 36, the user's wrist region is shown with all of the fasteners 20 secured and the outrigger guide assembly 126 removed.

Figure 37:
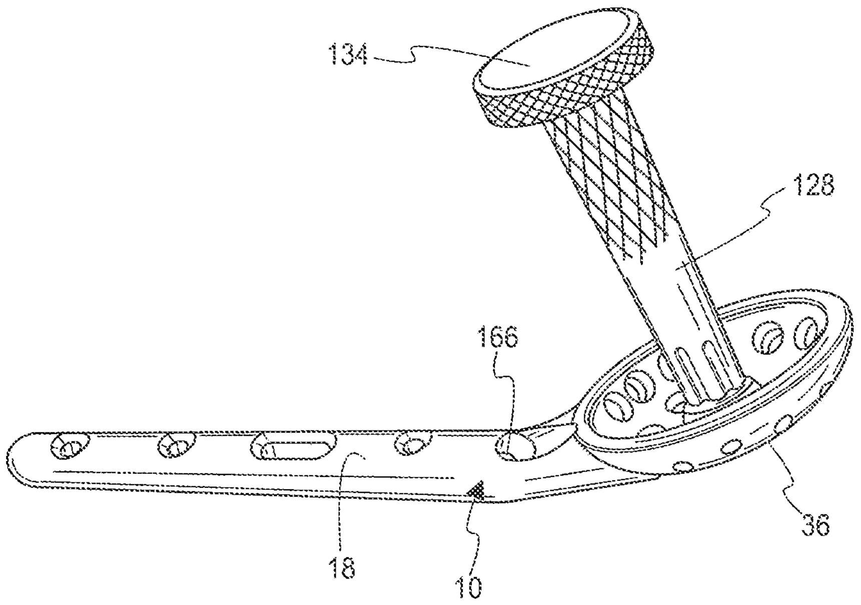
FIG. 37 is a perspective view of the inventive implant, as in FIGS. 4-9, and with a bracing component associated with the outrigger guide assembly releasably connected thereto.
Figure 38:
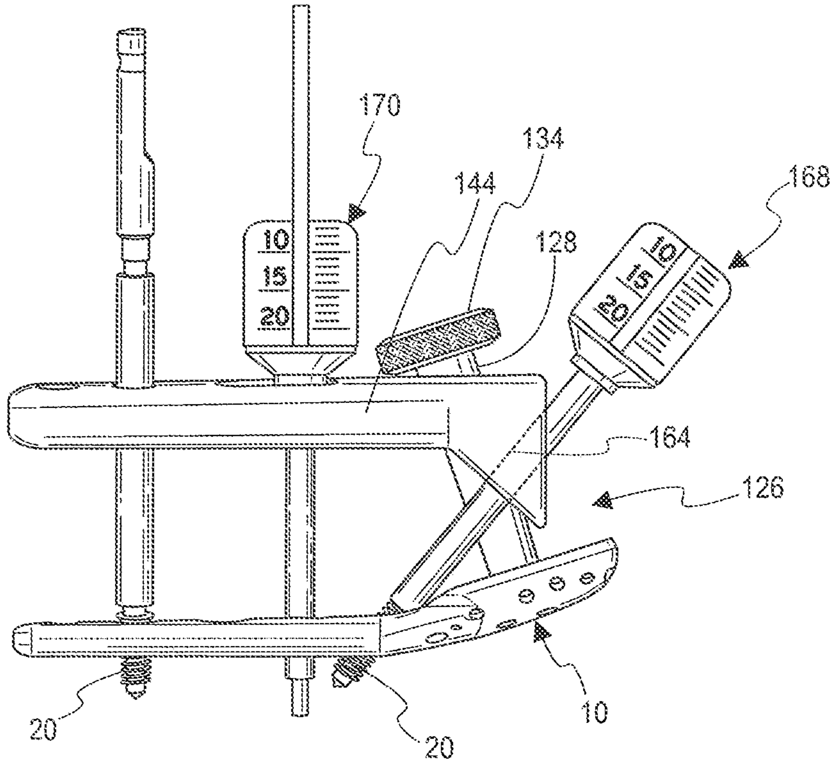
FIG. 38 is a side elevation view of the inventive implant in FIGS. 4-9 with the outrigger guide assembly in an operative relationship therewith.

In FIGS. 37 and 38, additional details of the outrigger guide assembly 126 are more clearly shown in relationship to the implant 10.

In FIG. 37, the first bracing component 128, which is an integral part of the outrigger guide assembly 126, is shown releasably fixed in place on the implant through the anchoring part 134 and without the elongate guide 144 thereon.

As seen in FIG. 38, the elongate guide 144 has a guide passage 164 which is aligned to create an opening in the radius 64 to accept a fastener 20 directed through an opening 166 at a region adjacent to where the stem 18 and cup-shaped wall 36 connect.

FIG. 38 also shows depth guides 168, 170 to facilitate controlled drilling of bone to accept the fasteners 20.

As noted above, the body 12 may include the body part 28 which may be appropriately fixed to one or more metacarpal bones. The body part 28 may overlie, and/or be inserted into, one or more of the metacarpal bones.

Figure 39:
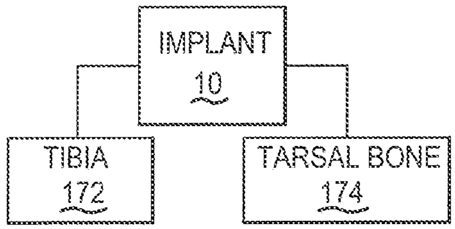
FIG. 39 is a schematic representation of an alternative use of the inventive implant for fusing a tibia and a tarsal bone.

As noted above, the inventive implant is not limited to use with wrist fusion applications. The same concepts can be employed to effect fusion at other anatomical locations. As just examples, as shown in FIG. 39, the implant 10 may be used to effect fusion between a tibia 172 and tarsal bone 174.

Figure 40:
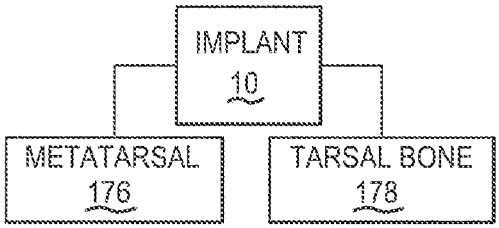
FIG. 40 is a schematic representation of the inventive implant as used to fuse a metatarsal and tarsal bone.

Alternatively, as shown in FIG. 40, the implant 10 may be used to effect fusion between a metatarsal 176 and tarsal bone 178.

In these particular applications, the stem 18 may be inserted into the tibia or metatarsal, with the cup-shaped wall 36 fixed to the tarsal bone.

Figure 7:
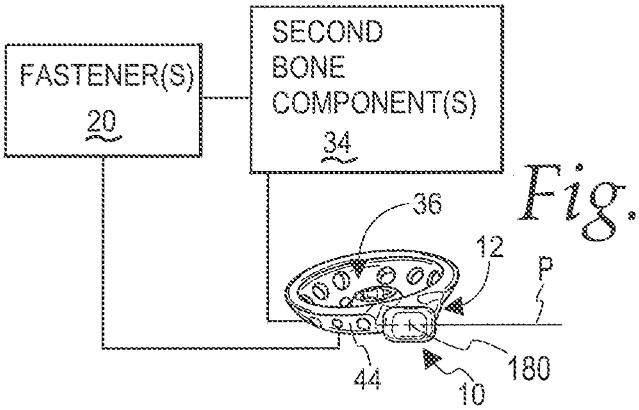
FIG. 7 is an end elevation view of the implant in FIGS. 4-6, together with a schematic depiction of an associated bone component to which one portion of the implant is fixed through one or more fasteners.
Figure 8:
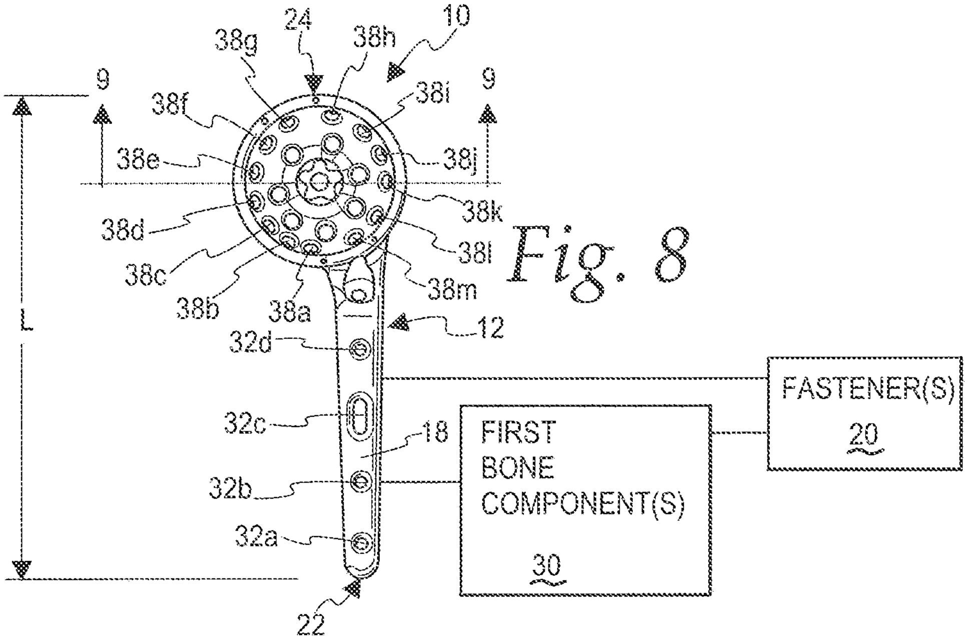
FIG. 8 is a view as in FIG. 6 with a schematic representation of a bone component to which another portion of the implant is fixed using one or more fasteners.

As seen in FIGS. 4, 7, and 9, the flat surface 50 on the bottom wall portion 48 is angled in two dimensions with respect to a reference plane P that approximates a flat profile of the stem 18 extending through a central, lengthwise axis 180 of the stem 18. In other words, the cup-shaped wall 36 is angled dorsally with respect to the plane of the patient's forearm, as well as angled rotationally in supination.

As seen in FIGS. 4, 7, and 9, the plane P is at an angle $\alpha$ with respect to a reference plane P1 containing the bottom wall surface 50, which in turn is substantially parallel to a reference plane P2 across the edge of the rim 46. In one preferred form, the angle $\alpha$ is on the order of at least 10°.

With fasteners securing the implant 10 to multiple bone components on opposite sides of the fusion site, the implant 10 is able to resist forces with large moment arms across the joint. At the same time, in the wrist application, situation of the stem 18 within the radius canal obviates the need to fix a plate that requires a complex curved implant, cutting of a channel for the plate, and the use of a bulky superficial plate. Since the carpus is centered over the joint surface of the distal radius, the stem 18 directly aligns with the cup-shaped wall 36.

As seen in exemplary FIG. 36, the second anchoring portion 16 is effectively recessed over its entire footprint so as not to add protruding mass that could cause discomfort, as from soft tissue irritation, and/or potentially damage to a patient such as tendon rupture or cosmetic deformity.

The ability to direct fasteners through the cup-shaped wall 36 at different angles reinforces the connection between the multiple bone components.

By reason of having complementary tapered cup shapes on the cup-shaped wall 36 and cavity 106, as the cup-shaped wall 36 is directed into the cavity 106, the convex surface 44 and surface bounding the cavity 106 cooperate to consistently guide the cup-shaped wall 36 into the cavity 106 wherein the second anchoring portion 16 realizes its operative position.

By reason of providing an implant that is centrally positioned close to the neutral axis of the exemplary radius, bending loads on the implant may be reduced compared to other conventional implants.

By reason of using the intramedullary construction and recessing to at least a certain extent the second anchoring portion 16, the inventive implant makes possible a reduction in: prominence of the implant; cosmetic deformity; soft tissue irritation; and tendon problems.

With the inventive structure, it is possible to provide a relatively short surgical incision to retain blood supply to the bone.

The inventive implant, as described above, can be made without a complex shape to fit a wide range of applications without the need for extensive bone carpentry or implant bending to avoid implant prominence at the surgical site. At the same time, the implant can be made with a significant vertical thickness providing bending strength and stiffness while avoiding soft tissue prominence.

With the inventive structure, it is possible to provide reliable fixation that does not necessarily require extending fixation and complication risk to unrelated regions, such as crossing the carpal-metacarpal joint and requiring screw placement into a metacarpal bone.

Further, the particular design as described herein, which is exemplary in nature only, provides sufficient multiplicity of fastener openings and a variable range of fastener angular placement into small bones that may be part of the fusion mass, such as into carpal bones.

The strategic use and placement of fasteners may also allow the same to be removed without requiring extensive destruction of bone.

The foregoing disclosure of specific embodiments is intended to be illustrative of the broad concepts comprehended by the invention.

The invention claimed is:

1. An implant for fusing at least two bone components that are different bones, the implant comprising:

a body comprising first and second anchoring portions and first and second spaced ends, the first anchoring portion comprising a stem at one of the first and second spaced ends of the body and configured to be directed to within a first bone component with the first anchoring portion in an operative position, the first anchoring portion configured to cooperate with at least a first fastener usable to cause the stem to be fixed relative to the first bone component with the first anchoring portion in its operative position, the second anchoring portion configured to be fixed to at least a second bone component, the second anchoring portion configured such that when in an operative position at least a portion of the second anchoring portion lies within a cavity with a predetermined shape produced in the at least second bone component, the second anchoring portion further configured to cooperate with at least a second fastener usable to fix a part of the second anchoring portion relative to the second bone component to thereby maintain the second anchoring portion in its operative position, wherein at least a part of the second anchoring portion has a cup-shaped wall at the other of the first and second spaced ends of the body which has a cup-shaped concave surface and an oppositely facing cup-shaped convex surface, the first anchoring portion extending away from the cup-shaped wall, the cup-shaped convex surface configured to be directed into the cavity in the at least second bone component so as to appose at least a part of a surface on the at least second bone component bounding the cavity, wherein the second anchoring portion has an opening through the cup-shaped wall and defined to accept the second fastener directed through the cup-shaped concave surface and the oppositely facing cup-shaped convex surface and into the second bone component to fix the part of the second anchoring portion relative to the second bone component, the implant for fusing at least two bone components provided in combination with a cutting tool to be operated to produce the predetermined cavity shape in the at least second bone component.

2. The combination according to claim 1 wherein the stem has an opening therein to cooperate with the first fastener usable to fix the stem relative to the first bone component and thereby maintain the first anchoring portion in its operative position.

3. The combination according to claim 2 further in combination with: a) the first fastener configured to extend into the first bone component and the stem opening to fix the stem relative to the first bone component; and b) the second fastener configured to extend through the opening in the second anchoring portion and into the second bone component to fix the part of the second anchoring portion relative to the second bone component.

4. The combination according to claim 1 wherein the body comprises a single rigid piece that defines the first and second anchoring portions.

5. The combination according to claim 1 wherein the body has an elongate shape with a length between the first and second spaced ends and a width, wherein the stem has a width that is substantially less than a width of the cup-shaped wall.

6. The combination according to claim 1 wherein the cup-shaped concave surface has a central axis, the body comprises an elongate portion defining the stem, the elongate portion extends away from the part of the second anchoring portion and has a lengthwise center line, and the lengthwise center line is offset from the central axis.

7. The combination according to claim 1 wherein the body is made from polyetheretherketone (PEEK).

8. The combination according to claim 1 wherein the body is made from a non-PEEK material that is one of metal and non-metal.

9. The combination according to claim 1 wherein the cup-shaped convex surface has an axis and an arcuate shape extending at least partially around the axis.

10. The combination according to claim 1 wherein the cutting tool comprises a reamer with a shaft that is turned to cause a cutting surface on the reamer to produce the predetermined cavity shape in the at least second bone component.

11. The combination according to claim 1 wherein the predetermined cavity shape is a cup shape.

12. The combination according to claim 1 wherein the stem has a plurality of openings therein each to cooperate with a fastener usable to fix the stem relative to the first bone component, and further in combination with an outrigger guide assembly that is releasably attachable to the implant and has guide openings to facilitate controlled formation of a plurality of openings in the first bone component, each alignable with one of the openings in the stem.

13. The combination according to claim 12 wherein one of the openings in the stem is elongate.

14. The combination according to claim 1 wherein the stem has a plurality of openings therein, each to cooperate with a fastener usable to fix the stem relative to the first bone component, and one of the openings in the stem is elongate.

15. An implant for fusing at least two bone components, the implant comprising:

a body comprising first and second anchoring portions, the first anchoring portion comprising a stem configured to be directed to within a first bone component with the first anchoring portion in an operative position, the first anchoring portion configured to cooperate with at least a first fastener usable to cause the stem to be fixed relative to the first bone component with the first anchoring portion in its operative position, the second anchoring portion configured to be fixed to at least a second bone component, the second anchoring portion configured such that when in an operative position at least a portion of the second anchoring portion lies within a cavity with a predetermined shape produced in the at least second bone component, the second anchoring portion further configured to cooperate with at least a second fastener usable to fix a part of the second anchoring portion relative to the second bone component to thereby maintain the second anchoring portion in its operative position, wherein the second anchoring portion has an opening therein through which the second fastener can extend to be directed into the second bone component to fix the part of the second anchoring portion relative to the second bone component, wherein the implant is provided in combination with the second fastener configured to extend through the opening in the second anchoring portion and into the second bone component to fix the part of the second anchoring portion relative to the second bone component, wherein the second anchoring portion has a cup-shaped surface, wherein the cup-shaped surface extends to a rim and there is a discrete cutout through the rim.

16. An implant for fusing at least two bone components that are different bones, the implant comprising:

a body comprising first and second anchoring portions and first and second spaced ends, the first anchoring portion comprising a stem at one of the first and second spaced ends of the body and configured to be directed to within a first bone component with the first anchoring portion in an operative position, the first anchoring portion configured to cooperate with at least a first fastener usable to cause the stem to be fixed relative to the first bone component with the first anchoring portion in its operative position, the second anchoring portion configured to be fixed to at least a second bone component, the second anchoring portion configured such that when in an operative position at least a portion of the second anchoring portion lies within a cavity with a predetermined shape produced in the at least second bone component, the second anchoring portion further configured to cooperate with at least a second fastener usable to fix a part of the second anchoring portion relative to the second bone component to thereby maintain the second anchoring portion in its operative position, wherein at least a part of the second anchoring portion has a cup-shaped wall at the other of the first and second spaced ends of the body which has a cup-shaped concave surface and an oppositely facing cup-shaped convex surface, the first anchoring portion extending away from the cup-shaped wall, the cup-shaped convex surface configured to be directed into the cavity in the at least second bone component so as to appose at least a part of a surface on the at least second bone component bounding the cavity, wherein the second anchoring portion has an opening through the cup-shaped wall and defined to accept the second fastener directed through the cup-shaped concave surface and the oppositely facing cup-shaped convex surface and into the second bone component to fix the part of the second anchoring portion relative to the second bone component, wherein the cup-shaped wall has a central axis and the convex outer surface is symmetrical around the central axis and tapers in an axial direction.

17. The implant for fusing at least two bone components according to claim 16 wherein the cup-shaped wall has a plurality of openings through which fasteners can be directed at different angles.

18. The implant for fusing at least two bone components according to claim 16 wherein the cup-shaped wall has a discrete receptacle therein for a quantity of bone graft material.

19. The implant for fusing at least two bone components according to claim 18 wherein the cup-shaped wall has at least a portion that is substantially flat and the discrete receptacle is formed in the substantially flat wall portion.

20. An implant for fusing at least two bone components that are different bones, the implant comprising:

a body comprising first and second anchoring portions and first and second spaced ends, the first anchoring portion comprising a stem at one of the first and second spaced ends of the body and configured to be directed to within a first bone component with the first anchoring portion in an operative position, the first anchoring portion configured to cooperate with at least a first fastener usable to cause the stem to be fixed relative to the first bone component with the first anchoring portion in its operative position, the second anchoring portion configured to be fixed to at least a second bone component, the second anchoring portion configured such that when in an operative position at least a portion of the second anchoring portion lies within a cavity with a predetermined shape produced in the at least second bone component, the second anchoring portion further configured to cooperate with at least a second fastener usable to fix a part of the second anchoring portion relative to the second bone component to thereby maintain the second anchoring portion in its operative position, wherein at least a part of the second anchoring portion has a cup-shaped wall at the other of the first and second spaced ends of the body which has a cup-shaped concave surface and an oppositely facing cup-shaped convex surface, the first anchoring portion extending away from the cup-shaped wall, the cup-shaped convex surface configured to be directed into the cavity in the at least second bone component so as to appose at least a part of a surface on the at least second bone component bounding the cavity, wherein the second anchoring portion has an opening through the cup-shaped wall and defined to accept the second fastener directed through the cup-shaped concave surface and the oppositely facing cup-shaped convex surface and into the second bone component to fix the part of the second anchoring portion relative to the second bone component, wherein the body has an elongate shape with a length between the spaced ends and a width, wherein the stem extends away from the cup-shaped wall to one of the body ends and another part of the body extends away from the cup-shaped wall at a location spaced from a location where the stem extends away from the part of the cup-shaped wall.

21. The implant for fusing at least two bone components according to claim 20 wherein the another part of the body extends away from the cup-shaped wall in a direction away from the first body end.

22. An implant for fusing at least two bone components, the implant comprising:

a body comprising first and second anchoring portions, the first anchoring portion comprising a stem configured to be directed to within a first bone component with the first anchoring portion in an operative position, the first anchoring portion configured to cooperate with at least a first fastener usable to cause the stem to be fixed relative to the first bone component with the first anchoring portion in its operative position, the second anchoring portion configured to be fixed to at least a second bone component, the second anchoring portion configured such that when in an operative position at least a portion of the second anchoring portion lies within a cavity produced in the at least second bone component, the second anchoring portion further configured to cooperate with at least a second fastener usable to fix a part of the second anchoring portion relative to the second bone component to thereby maintain the second anchoring portion in its operative position, wherein the stem has an elongate shape with a central axis and a flat profile approximated by a reference plane containing the central axis, the second anchoring portion has a cup-shaped wall with a substantially flat surface to bear against the second bone component with the second anchoring portion in its operative position and the flat surface of the cup-shaped wall is angled in two dimensions with respect to the reference plane.

23. An implant for fusing at least two bone components, the implant comprising:

a body comprising first and second anchoring portions, the first anchoring portion comprising a stem configured to be directed to within a first bone component with the first anchoring portion in an operative position, the first anchoring portion configured to cooperate with at least a first fastener usable to cause the stem to be fixed relative to the first bone component with the first anchoring portion in its operative position, the second anchoring portion configured to be fixed to at least a second bone component, the second anchoring portion configured such that when in an operative position at least a portion of the second anchoring portion lies within a cavity produced in the at least second bone component, the second anchoring portion further configured to cooperate with at least a second fastener usable to fix a part of the second anchoring portion relative to the second bone component to thereby maintain the second anchoring portion in its operative position, wherein the second anchoring portion has a surface that has at least a portion with a convex shape to be directed into the cavity in the at least second bone component so as to appose at least a part of the surface on the at least second bone component bounding the cavity, wherein the second anchoring portion comprises a cup-shaped wall with a bottom wall portion at which a first connector is provided, said implant provided in combination with a first bracing component with a second connector, the first and second connectors configured to be joinable to releasably maintain the first bracing component in an operative position on the implant.

24. The implant for fusing at least two bone components according to claim 23 wherein the cup-shaped wall has an axis and the first bracing component is elongate with a length and with the first bracing component in its operative position, the length of the first bracing component aligns with the axis of the cup-shaped wall.

25. The combination according to claim 23 further in combination with a second bracing component configured to be connected to the first bone component.

26. The combination according to claim 25 wherein the stem has an elongate opening therein through which the second bracing component can be extended.

27. The combination according to claim 26 further in combination with a tool for engaging the first and second bracing components and urging the first and second bracing components towards each other.

28. An implant for fusing at least two bone components, the implant comprising:

a body comprising first and second anchoring portions, the first anchoring portion comprising a stem configured to be directed to within a first bone component with the first anchoring portion in an operative position, the first anchoring portion configured to cooperate with at least a first fastener usable to cause the stem to be fixed relative to the first bone component with the first anchoring portion in its operative position, the second anchoring portion configured to be fixed to at least a second bone component, the second anchoring portion configured such that when in an operative position at least a portion of the second anchoring portion lies within a cavity with a predetermined shape produced in the at least second bone component, the second anchoring portion further configured to cooperate with at least a second fastener usable to fix a part of the second anchoring portion relative to the second bone component to thereby maintain the second anchoring portion in its operative position, wherein the second anchoring portion has an opening therein through which the second fastener can extend to be directed into the second bone component to fix the part of the second anchoring portion relative to the second bone component, wherein the implant is provided in combination with the second fastener configured to extend through the opening in the second anchoring portion and into the second bone component to fix the part of the second anchoring portion relative to the second bone component, wherein the stem has a plurality of openings therein each to cooperate with a fastener usable to fix the stem relative to the first bone component, and further in combination with an outrigger guide assembly that is releasably attachable to the implant and has guide openings to facilitate controlled formation of a plurality of openings in the first bone component, each alignable with one of the openings in the stem, wherein one of the openings in the stem is elongate, further in combination with a first bracing component, wherein the outrigger guide assembly is configured to facilitate formation of a first of the plurality of openings in the first bone component such that the first bracing component can be directed into the first of the plurality of openings in the first bone component and the one elongate stem opening at one end thereof to allow the implant to shift relative to the first bracing component to thereby reside at an opposite end of the one elongate stem opening.

29. A method of fusing bone components that are different bones, the method comprising the steps of:

obtaining an implant comprising:

a body comprising first and second anchoring portions, the first anchoring portion comprising a stem configured to be directed to within a first bone component with the first anchoring portion in an operative position, the first anchoring portion configured to cooperate with at least a first fastener usable to cause the stem to be fixed relative to the first bone component with the first anchoring portion in its operative position, the second anchoring portion configured to be fixed to at least a second bone component and having a cup-shaped wall which has a cup-shaped concave surface and an oppositely facing cup-shaped convex surface, the second anchoring portion configured such that when in an operative position at least a portion of the second anchoring portion including the cup-shaped convex surface lies within a cavity produced in the at least second bone component, the second anchoring portion further configured to cooperate with at least a second fastener usable to fix a part of the second anchoring portion relative to the second bone component to thereby maintain the second anchoring portion in its operative position;

directing the stem to within the first bone component to place the first anchoring component in its operative position;

fixing the stem in its operative position using at least a first fastener;

strategically removing bone from at least a second bone component to define a cavity at a placement location for the second anchoring portion;

placing the second anchoring portion in its operative position wherein at least a part of the second anchoring portion overlies the at least second bone component at the placement location; and fixing the second anchoring portion in its operative position using at least a second fastener directed through the cup-shaped convex surface and the oppositely facing cup-shaped concave surface on the second anchoring portion and into the second bone component, wherein the step of strategically removing bone comprises removing bone to define the cavity at the placement location with a shape that is complementary to the part of the second anchoring portion that overlies the placement location, wherein the cavity at the placement location has a tapered shape and the step of placing the second anchoring portion comprises directing a part of the second anchoring portion into the cavity so that at least one bone surface surrounding the cavity cooperates with a part of the second anchoring portion to consistently guide the second anchoring portion into its operative position.

30. The method of fusing bone components according to claim 29 wherein the first bone component is a radius bone and the second bone component is a carpal bone.

31. The method of fusing bone components according to claim 29 wherein the at least second bone component comprises multiple carpal bones.

32. The method of fusing bone components according to claim 29 wherein the step of strategically removing bone comprises removing bone using a reamer with a rotary cutting surface.

33. The method of fusing bone components according to claim 32 wherein the step of using a reamer comprises using the reamer so that the rotary cutting surface removes bone simultaneously from a plurality of bone components.

34. The method of fusing bone components according to claim 32 wherein the rotary cutting surface is configured to produce a cup-shaped cavity and has a pilot extension.

35. The method of fusing bone components according to claim 34 further comprising the step of forming a pilot bore in the at least second bone component.

36. The method of fusing bone components according to claim 29 further comprising the step of placing bone graft material between the second anchoring portion and bone at the placement location.

37. The method of fusing bone components according to claim 29 wherein the first bone component is a tibia and the at least second bone component is a tarsal bone.

38. The method of fusing bone components according to claim 29 wherein the first bone component is a metatarsal and the second bone component is a tarsal bone.

39. The method of fusing bone components according to claim 29 wherein the step of strategically removing bone comprises removing bone in a manner to allow the part of the second anchoring portion that overlies the placement location to be recessed in the cavity at the placement location.

40. The method of fusing bone components according to claim 39 wherein with the second anchoring portion in its operative position the convex surface on the second anchoring portion is situated so as to appose a concave surface defining the tapered shape bounding the cavity.

41. The method of fusing bone components according to claim 29 wherein the step of fixing the second anchoring portion comprises directing a plurality of fasteners through the cup-shaped wall into different bone components.

42. The method of fusing bone components according to claim 41 wherein at least two of the plurality of fasteners are directed into the different bone components at different angles.

43. The method of fusing bone components according to claim 29 further comprising the steps of:

broaching the first bone component with a broaching tool; and after broaching the first bone component, separating the broaching tool from the first bone component and directing the stem to within the first bone component.

44. The method of fusing bone components according to claim 29 further comprising the step of provisionally securing the second anchoring portion in its operative position with temporary fasteners before using the at least first fastener.

45. The method of fusing bone components according to claim 29 further comprising the step of stabilizing the first bone component and the second bone component before strategically removing bone from the at least second bone component.

46. A method of fusing bone components that are different bones, the method comprising the steps of:

obtaining an implant comprising:

a body comprising first and second anchoring portions, the first anchoring portion comprising a stem configured to be directed to within a first bone component with the first anchoring portion in an operative position, the first anchoring portion configured to cooperate with at least a first fastener usable to cause the stem to be fixed relative to the first bone component with the first anchoring portion in its operative position, the second anchoring portion configured to be fixed to at least a second bone component and having a cup-shaped wall which has a cup-shaped concave surface and an oppositely facing cup-shaped convex surface, the second anchoring portion configured such that when in an operative position at least a portion of the second anchoring portion including the cup-shaped convex surface lies within a cavity produced in the at least second bone component, the second anchoring portion further configured to cooperate with at least a second fastener usable to fix a part of the second anchoring portion relative to the second bone component to thereby maintain the second anchoring portion in its operative position;

directing the stem to within the first bone component to place the first anchoring component in its operative position;

fixing the stem in its operative position using at least a first fastener;

strategically removing bone from at least a second bone component to define a cavity at a placement location for the second anchoring portion;

placing the second anchoring portion in its operative position wherein at least a part of the second anchoring portion overlies the at least second bone component at the placement location; and fixing the second anchoring portion in its operative position using at least a second fastener directed through the cup-shaped convex surface and the oppositely facing cup-shaped concave surface on the second anchoring portion and into the second bone component, wherein the step of strategically removing bone comprises removing bone to define the cavity at the placement location with a shape that is complementary to the part of the second anchoring portion that overlies the placement location, wherein the cavity at the placement location has a tapered shape and the step of placing the second anchoring portion comprises directing a part of the second anchoring portion into the cavity so that at least one bone surface surrounding the cavity cooperates with a part of the second anchoring portion to consistently guide the second anchoring portion into its operative position, wherein the step of strategically removing bone comprises removing bone from the first bone component at another placement location and with the second anchoring portion in its operative position the second anchoring portion overlies the another placement location.

47. A method of fusing bone components, the method comprising the steps of:

obtaining an implant comprising:

a body comprising first and second anchoring portions, the first anchoring portion comprising a stem configured to be directed to within a first bone component with the first anchoring portion in an operative position, the first anchoring portion configured to cooperate with at least a first fastener usable to cause the stem to be fixed relative to the first bone component with the first anchoring portion in its operative position, the second anchoring portion configured to be fixed to at least a second bone component, the second anchoring portion configured such that when in an operative position at least a portion of the second anchoring portion lies within a cavity produced in the at least second bone component, the second anchoring portion further configured to cooperate with at least a second fastener usable to fix a part of the second anchoring portion relative to the second bone component to thereby maintain the second anchoring portion in its operative position;

directing the stem to within the first bone component to place the first anchoring component in its operative position;

fixing the stem in its operative position using at least a first fastener;

strategically removing bone from at least a second bone component to define a cavity at a placement location for the second anchoring portion;

placing the second anchoring portion in its operative position wherein at least a part of the second anchoring portion overlies the at least second bone component at the placement location; and fixing the second anchoring portion in its operative position using at least a second fastener, wherein the step of strategically removing bone comprises removing bone to define the cavity at the placement location with a shape that is complementary to the part of the second anchoring portion that overlies the placement location, wherein the cavity at the placement location has a tapered shape and the step of placing the second anchoring portion comprises directing a part of the second anchoring portion into the cavity so that at least one bone surface surrounding the cavity cooperates with a part of the second anchoring portion to consistently guide the second anchoring portion into its operative position, wherein the first bone component is a radius bone and the second bone component is a carpal bone, wherein the second anchoring portion has a discrete cutout therein and further including the step of fixing the second anchoring portion in its operative position with the cutout located to avoid impingement of a radial ulnar joint by the implant.

48. A method of fusing bone components the method comprising the steps of:

obtaining an implant comprising:

a body comprising first and second anchoring portions, the first anchoring portion comprising a stem configured to be directed to within a first bone component with the first anchoring portion in an operative position, the first anchoring portion configured to cooperate with at least a first fastener usable to cause the stem to be fixed relative to the first bone component with the first anchoring portion in its operative position, the second anchoring portion configured to be fixed to at least a second bone component, the second anchoring portion configured such that when in an operative position at least a portion of the second anchoring portion lies within a cavity produced in the at least second bone component, the second anchoring portion further configured to cooperate with at least a second fastener usable to fix a part of the second anchoring portion relative to the second bone component to thereby maintain the second anchoring portion in its operative position;

directing the stem to within the first bone component to place the first anchoring component in its operative position;

fixing the stem in its operative position using at least a first fastener, strategically removing bone from at least a second bone component to define a cavity at a placement location for the second anchoring portion;

placing the second anchoring portion in its operative position wherein at least a part of the second anchoring portion overlies the at least second bone component at the placement location;

fixing the second anchoring portion in its operative position using at least a second fastener;

connecting a first bracing component to the implant;

directing a second bracing component through an elongate opening in the first anchoring portion and into the first bone component; and exerting a force tending to draw the first and second bracing components towards each other, whereby the second bracing component moves within the elongate opening and the first bone component and at least second bone component are urged towards each other into a desired relationship.

49. The method of fusing bone components according to claim 48 wherein the step of fixing the stem in its operative position comprises directing the first fastener into the first bone component and stem after the first bone component and at least second bone component are placed in the desired relationship.

50. A method of fusing bone components, the method comprising the steps of:

obtaining an implant comprising:

a body comprising first and second anchoring portions, the first anchoring portion comprising a stem configured to be directed to within a first bone component with the first anchoring portion in an operative position, the first anchoring portion configured to cooperate with at least a first fastener usable to cause the stem to be fixed relative to the first bone component with the first anchoring portion in its operative position, the second anchoring portion configured to be fixed to at least a second bone component, the second anchoring portion configured such that when in an operative position at least a portion of the second anchoring portion lies within a cavity produced in the at least second bone component, the second anchoring portion further configured to cooperate with at least a second fastener usable to fix a part of the second anchoring portion relative to the second bone component to thereby maintain the second anchoring portion in its operative position;

directing the stem to within the first bone component to place the first anchoring component in its operative position;

fixing the stem in its operative position using at least a first fastener;

strategically removing bone from at least a second bone component to define a cavity at a placement location for the second anchoring portion;

placing the second anchoring portion in its operative position wherein at least a part of the second anchoring portion overlies the at least second bone component at the placement location;

fixing the second anchoring portion in its operative position using at least a second fastener, wherein the step of strategically removing bone comprises removing bone using a reamer with a rotary cutting surface, wherein the rotary cutting surface is configured to produce a cup-shaped cavity and has a pilot extension;

forming a pilot bore in the at least second bone component; and releasably connecting a guide to the second anchoring portion, wherein the step of placing the second anchoring portion in its operative position comprises directing a part of the guide into the pilot bore to consistently guide the second anchoring portion into its operative position.

51. A method of fusing bone components, the method comprising the steps of:

obtaining an implant comprising:

a body comprising first and second anchoring portions, the first anchoring portion comprising a stem configured to be directed to within a first bone component with the first anchoring portion in an operative position, the first anchoring portion configured to cooperate with at least a first fastener usable to cause the stem to be fixed relative to the first bone component with the first anchoring portion in its operative position, the second anchoring portion configured to be fixed to at least a second bone component, the second anchoring portion configured such that when in an operative position at least a portion of the second anchoring portion lies within a cavity produced in the at least second bone component, the second anchoring portion further configured to cooperate with at least a second fastener usable to fix a part of the second anchoring portion relative to the second bone component to thereby maintain the second anchoring portion in its operative position;

directing the stem to within the first bone component to place the first anchoring component in its operative position;

fixing the stem in its operative position using at least a first fastener;

strategically removing bone from at least a second bone component to define a cavity at a placement location for the second anchoring portion;

placing the second anchoring portion in its operative position wherein at least a part of the second anchoring portion overlies the at least second bone component at the placement location;

fixing the second anchoring portion in its operative position using at least a second fastener;

broaching the first bone component with a broaching tool;

after broaching the first bone component, separating the broaching tool from the first bone component and directing the stem to within the first bone component; and using the broaching tool as a guide to form a pilot bore in the at least second bone component.

* * * * *